(12) United States Patent
Klein et al.

(10) Patent No.: US 10,751,451 B2
(45) Date of Patent: Aug. 25, 2020

(54) SURGICAL FLUID MANAGEMENT SYSTEMS AND METHODS

(71) Applicant: BOSTON SCIENTIFIC SCIMED, INC., Maple Grove, MN (US)

(72) Inventors: Kyle Klein, San Jose, CA (US); Aaron Germain, Campbell, CA (US); Csaba Truckai, Saratoga, CA (US); Michael D. Walker, San Francisco, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 259 days.

(21) Appl. No.: 15/876,403

(22) Filed: Jan. 22, 2018

(65) Prior Publication Data

US 2018/0140756 A1    May 24, 2018

Related U.S. Application Data

(63) Continuation of application No. 14/800,121, filed on Jul. 15, 2015, now Pat. No. 9,901,665, which is a
(Continued)

(51) Int. Cl.
*A61M 1/00* (2006.01)
*A61B 18/14* (2006.01)
(Continued)

(52) U.S. Cl.
CPC .......... *A61M 1/0064* (2013.01); *A61B 17/32* (2013.01); *A61B 17/32002* (2013.01);
(Continued)

(58) Field of Classification Search
CPC .. A61M 1/0056; A61M 1/006; A61M 1/0064; A61M 2202/0021;
(Continued)

(56) References Cited

U.S. PATENT DOCUMENTS 3,770,129 A    11/1973  Brumfield et al.
4,650,462 A     3/1987  DeSatnick et al.
(Continued)

FOREIGN PATENT DOCUMENTS

EP    0153190 A1    8/1985
EP    0331505 A1    9/1989
(Continued)

OTHER PUBLICATIONS

AAGL Practice Report: Practice Guidelines for the Management of Hysteroscopic Distending Media: (Replaces Hlysteroscopic Fluid Monitoring Guidelines. J Am Assoc Gynecol Laparosc. 2000;7: 167-168) J Minim Invasive Gynecol. Mar.-Apr. 2013;20:137-48. doi: 10.1016/j.jmig.2012.12.002.
(Continued)

*Primary Examiner* — Quynh-Nhu H. Vu
(74) *Attorney, Agent, or Firm* — Seager, Tufte & Wickhem, LLP

(57) ABSTRACT

A surgical fluid management system delivers fluid for distending a uterine cavity to allow cutting and extraction of uterine fibroid tissue, polyps and other abnormal uterine tissue. The system comprises a fluid source, fluid deliver lines, one or more pumps, and a filter for re-circulating the distension fluid between the source and the uterine cavity. A controller can monitor fluid retention by the patient.

20 Claims, 19 Drawing Sheets

Related U.S. Application Data continuation of application No. 13/624,760, filed on Sep. 21, 2012, now Pat. No. 9,084,847.

(60) Provisional application No. 61/597,000, filed on Feb. 9, 2012, provisional application No. 61/539,865, filed on Sep. 27, 2011, provisional application No. 61/538,034, filed on Sep. 22, 2011.

(51) Int. Cl.
| | |
|---|---|
| *A61M 3/02* | (2006.01) |
| *A61B 17/32* | (2006.01) |
| *A61B 1/012* | (2006.01) |
| *A61B 1/303* | (2006.01) |
| *A61B 17/42* | (2006.01) |
| *A61B 90/00* | (2016.01) |
| *A61B 18/00* | (2006.01) |
| *A61B 18/12* | (2006.01) |
| *A61B 18/16* | (2006.01) |

(52) U.S. Cl.
CPC ......... *A61B 18/1485* (2013.01); *A61M 1/006* (2014.02); *A61M 3/022* (2014.02); *A61M 3/0208* (2014.02); *A61M 3/0212* (2014.02); *A61M 3/0229* (2013.01); *A61B 1/012* (2013.01); *A61B 1/303* (2013.01); *A61B 2017/4216* (2013.01); *A61B 2018/00559* (2013.01); *A61B 2018/00601* (2013.01); *A61B 2018/00625* (2013.01); *A61B 2018/1213* (2013.01); *A61B 2018/162* (2013.01); *A61B 2090/064* (2016.02); *A61B 2217/005* (2013.01); *A61B 2217/007* (2013.01); *A61M 1/0056* (2013.01); *A61M 3/0266* (2013.01); *A61M 2202/0021* (2013.01); *A61M 2202/0028* (2013.01); *A61M 2205/3344* (2013.01); *A61M 2205/75* (2013.01); *A61M 2205/7545* (2013.01); *A61M 2210/1433* (2013.01)

(58) Field of Classification Search
CPC .. A61M 2202/0028; A61M 2205/3344; A61M 2205/75; A61M 2205/7545; A61M 2210/1433; A61M 3/0229; A61M 3/0266; A61B 17/32; A61B 17/32002; A61B 18/1485; A61B 1/012; A61B 1/303; A61B 2017/4216; A61B 2018/00559; 2018/00601; A61B 2018/00625; A61B 2018/1213; A61B 2018/162; A61B 1090/064; A61B 2217/005; A61B 2217/007

See application file for complete search history.

(56) References Cited

U.S. PATENT DOCUMENTS

| | | |
|---|---|---|
| 4,735,603 A | 4/1988 | Goodson et al. |
| 4,921,477 A | 5/1990 | Davis |
| 4,971,034 A | 11/1990 | Doi et al. |
| 4,998,527 A | 3/1991 | Meyer |
| 5,098,375 A | 3/1992 | Baier |
| 5,106,364 A | 4/1992 | Hayafuji et al. |
| 5,169,397 A | 12/1992 | Sakashita et al. |
| 5,277,696 A | 1/1994 | Hagen et al. |
| 5,312,399 A | 5/1994 | Hakky et al. |
| 5,320,091 A | 6/1994 | Grossi et al. |
| 5,382,229 A * | 1/1995 | Grabenkort ......... A61M 1/0058 604/27 |
| 5,437,629 A | 8/1995 | Goldrath |
| 5,456,689 A | 10/1995 | Kresch et al. |
| 5,476,447 A | 12/1995 | Noda et al. |
| 5,527,331 A | 6/1996 | Kresch et al. |
| 5,626,563 A | 5/1997 | Dodge et al. |
| 5,643,203 A | 7/1997 | Beiser et al. |
| 5,669,921 A | 9/1997 | Berman et al. |
| 5,730,752 A | 3/1998 | Alden et al. |
| 5,779,662 A | 7/1998 | Berman |
| 5,810,858 A | 9/1998 | Berman et al. |
| 5,823,990 A | 10/1998 | Henley et al. |
| 5,830,180 A | 11/1998 | Chandler et al. |
| 5,853,392 A | 12/1998 | Dennis |
| 5,906,615 A | 5/1999 | Thompson |
| 5,925,050 A | 7/1999 | Howard, III |
| 6,032,673 A | 3/2000 | Savage et al. |
| 6,109,268 A | 8/2000 | Thapliyal et al. |
| RE36,914 E | 10/2000 | Carlsen et al. |
| 6,206,014 B1 | 3/2001 | Cameron, III et al. |
| 6,245,084 B1 | 6/2001 | Mark et al. |
| 6,302,864 B1 | 10/2001 | Nowosielski |
| 6,358,263 B2 | 3/2002 | Mark et al. |
| 6,428,316 B1 | 8/2002 | Rodriquez |
| 6,432,113 B1 | 8/2002 | Parkin et al. |
| 6,629,986 B1 | 10/2003 | Ross et al. |
| 6,972,009 B1 | 12/2005 | Stromberg et al. |
| 7,029,451 B2 | 4/2006 | Anderson et al. |
| 7,070,604 B1 | 7/2006 | Garito et al. |
| 7,204,821 B1 | 4/2007 | Clare et al. |
| 7,226,459 B2 | 6/2007 | Cesarini et al. |
| 7,384,417 B2 | 6/2008 | Cucin |
| 7,549,987 B2 | 6/2009 | Shadduck |
| 7,674,259 B2 | 3/2010 | Shadduck |
| 7,892,229 B2 | 2/2011 | Shadduck et al. |
| 8,061,359 B2 | 11/2011 | Emanuel |
| 8,313,485 B2 | 11/2012 | Shadduck |
| 8,512,326 B2 | 8/2013 | Shadduck et al. |
| 8,568,424 B2 | 10/2013 | Shugrue et al. |
| 8,574,253 B2 | 11/2013 | Gruber et al. |
| 8,728,066 B2 | 5/2014 | Shadduck et al. |
| 8,840,625 B2 | 9/2014 | Adams et al. |
| 8,840,626 B2 | 9/2014 | Adams et al. |
| 8,951,274 B2 | 2/2015 | Adams et al. |
| 9,072,431 B2 | 7/2015 | Adams et al. |
| 9,095,366 B2 | 8/2015 | Sullivan et al. |
| 9,233,193 B2 | 1/2016 | Truckai et al. |
| 2002/0010463 A1 | 1/2002 | Mulier et al. |
| 2002/0032403 A1* | 3/2002 | Savagle ............. A61M 3/0258 604/28 |
| 2002/0072745 A1 | 6/2002 | Truckai et al. |
| 2003/0060862 A1 | 3/2003 | Goble et al. |
| 2003/0176833 A1* | 9/2003 | Libermann ......... A61M 3/0241 604/65 |
| 2004/0049217 A1 | 3/2004 | Ross et al. |
| 2004/0092980 A1 | 5/2004 | Cesarini et al. |
| 2004/0102770 A1 | 5/2004 | Goble |
| 2004/0167427 A1 | 8/2004 | Quick et al. |
| 2004/0167428 A1 | 8/2004 | Quick et al. |
| 2004/0267255 A1 | 12/2004 | Auge, II et al. |
| 2005/0096649 A1 | 5/2005 | Adams |
| 2005/0119628 A1 | 6/2005 | Sant et al. |
| 2005/0236329 A1 | 10/2005 | Brotherton et al. |
| 2006/0047185 A1 | 3/2006 | Shener et al. |
| 2006/0135955 A1 | 6/2006 | Shadduck |
| 2006/0200064 A1 | 9/2006 | Gross et al. |
| 2006/0224154 A1 | 10/2006 | Shadduck et al. |
| 2007/0016182 A1 | 1/2007 | Lipson et al. |
| 2007/0021713 A1 | 1/2007 | Kumar et al. |
| 2007/0036768 A1 | 2/2007 | Fraser et al. |
| 2007/0088275 A1 | 4/2007 | Stearns et al. |
| 2007/0123838 A1 | 5/2007 | Bernard et al. |
| 2007/0181499 A1 | 8/2007 | Roberts et al. |
| 2007/0244353 A1 | 10/2007 | Larsen |
| 2008/0039832 A1 | 2/2008 | Palanker et al. |
| 2008/0065060 A1 | 3/2008 | Ein-Gal |
| 2008/0071269 A1 | 3/2008 | Hilario et al. |
| 2008/0091061 A1 | 4/2008 | Kumar et al. |
| 2008/0091071 A1 | 4/2008 | Kumar et al. |
| 2008/0097468 A1 | 4/2008 | Adams et al. |
| 2008/0097471 A1 | 4/2008 | Adams et al. |
| 2008/0287893 A1 | 11/2008 | Ineson |
| 2009/0043238 A1 | 2/2009 | Lane et al. |

(56) References Cited

U.S. PATENT DOCUMENTS

| | | |
|---|---|---|
| 2009/0082715 A1 | 3/2009 | Charles |
| 2009/0137943 A1 | 5/2009 | Stearns et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2009/0312753 A1 | 12/2009 | Shadduck |
| 2010/0100091 A1 | 4/2010 | Truckai |
| 2010/0152533 A1 | 6/2010 | Mark |
| 2010/0234797 A1* | 9/2010 | Gelfand .............. A61B 5/201 604/66 |
| 2011/0060273 A1 | 3/2011 | Ofsthun et al. |
| 2011/0224486 A1 | 9/2011 | Nguyen et al. |
| 2011/0264090 A1 | 10/2011 | Sahdduck et al. |
| 2011/0306968 A1 | 12/2011 | Beckman et al. |
| 2012/0010464 A1 | 1/2012 | Adams et al. |
| 2012/0053583 A1 | 3/2012 | Palanker et al. |
| 2012/0172888 A1 | 7/2012 | Shugrue et al. |
| 2012/0172889 A1 | 7/2012 | Chin et al. |
| 2012/0271300 A9 | 10/2012 | Shadduck et al. |
| 2012/0330292 A1 | 12/2012 | Shadduck et al. |
| 2013/0046304 A1 | 2/2013 | Germain et al. |
| 2013/0079702 A1 | 3/2013 | Klein et al. |
| 2013/0103021 A1 | 4/2013 | Germain et al. |
| 2013/0172805 A1 | 7/2013 | Truckai et al. |
| 2013/0172870 A1 | 7/2013 | Germain et al. |
| 2013/0231652 A1 | 9/2013 | Germain et al. |
| 2013/0296847 A1 | 11/2013 | Germain et al. |
| 2014/0303551 A1 | 10/2014 | Germain et al. |
| 2014/0324065 A1 | 10/2014 | Bek et al. |
| 2015/0119795 A1 | 4/2015 | Germain et al. |
| 2015/0328379 A1* | 11/2015 | Carr .............. A61M 1/0007 604/28 |

FOREIGN PATENT DOCUMENTS

| | | |
|---|---|---|
| EP | 2100567 A1 | 9/2009 |
| GB | 2296869 A | 7/1996 |
| GB | 2327351 A | 1/1999 |
| JP | 1989087708 | 6/1989 |
| JP | 2008511397 A | 4/2008 |
| JP | 2011212450 A | 10/2011 |
| WO | 2004043313 A2 | 5/2004 |
| WO | 2005037088 A2 | 4/2005 |
| WO | 2010096139 A2 | 8/2010 |
| WO | 2011060189 A1 | 5/2011 |
| WO | 2010096139 A3 | 12/2011 |
| WO | 2013003570 A1 | 1/2013 |

OTHER PUBLICATIONS

International search report and written opinion dated Oct. 16, 2012 for PCT/US2012/044609.

International search report and written opinion dated Dec. 4, 2012 for PCT/US2012/056936.

Liu, et al. Clinical application of hysteriscopic electroresection in 775 cases. Di YHi Jun Yi Da Xue Xue Bao. Apr. 2004;24(4):467-9. (in Chinese with English abstract).

Phillips, et al. The Effect of Dilute Vasopressin Solution on Blood Loss During Operative Hysteroscopy. J Am Assoc Gynecol Laparosc. Aug. 1996;3(4, Supplement):S38.

* cited by examiner

SURGICAL FLUID MANAGEMENT SYSTEMS AND METHODS

CROSS REFERENCE TO RELATED APPLICATIONS

This application is a continuation of U.S. patent application Ser. No. 14/800,121, filed Jul. 15, 2015, which is a continuation of U.S. patent application Ser. No. 13/624,760, filed Sep. 21, 2012, now U.S. Pat. No. 9,084,847, which application claims the benefit of U.S. Provisional Application No. 61/538,034, filed Sep. 22, 2011, U.S. Provisional Application No. 61/539,865, filed Sep. 27, 2011, and U.S. Provisional Application No. 61/597,000, filed Feb. 9, 2012, the entire contents of which are incorporated herein by reference in their entirety.

FIELD OF INVENTION

The present invention relates surgical fluid management systems and methods, for example for use in distending the uterine cavity to allow cutting and extraction of uterine fibroid tissue, polyps and other abnormal uterine tissue.

BACKGROUND OF INVENTION

Uterine fibroids are non-cancerous tumors that develop in the wall of uterus. Such fibroids occur in a large percentage of the female population, with some studies indicating up to 40 percent of all women have fibroids. Uterine fibroids can grow over time to be several centimeters in diameter and symptoms can include menorrhagia, reproductive dysfunction, pelvic pressure and pain.

One current treatment of fibroids is hysteroscopic resection or myomectomy which involves transcervical access to the uterus with a hysteroscope together with insertion of a cutting instrument through a working channel in the hysteroscope. The cutting instrument may be a mechanical tissue cutter or an electrosurgical resection device such as a cutting loop. Mechanical cutting devices are disclosed in U.S. Pat. Nos. 7,226,459; 6,032,673 and 5,730,752 and U.S. Published Patent Appl. 2009/0270898. An electrosurgical cutting device is disclosed in U.S. Pat. No. 5,906,615.

In a myomectomy or hysteroscopic resection, the initial step of the procedure includes distention of the uterine cavity to create a working space for assisting viewing through the hysteroscope. In a relaxed state, the uterine cavity collapses with the uterine walls in contact with one another. A fluid management system is used to distend the uterus to provide a working space wherein a fluid is administered through a passageway in the hysteroscope under sufficient pressure to expand or distend the uterine cavity. The fluids used to distend the uterus are typically liquid aqueous solutions such as a saline solution or a sugar-based aqueous solution.

In some RF electrosurgical resection procedures, the distending fluid is a non-conductive aqueous solution to limit RF current conduction.

One particular concern is the fact that fluid management systems typically administer the fluid under a pressure of up to 100 mm Hg or more which results in a significant risk that the distending fluid may be taken up by a cut blood vessel exposed in the uterine cavity. Such unwanted fluid uptake is known as intravasation, which can lead to serious complications and even death. For this reason, fluid management systems have been developed to monitor the patient's fluid uptake on a continuous basis during a procedure, typically using complicated systems that capture, collect and weigh distending fluids that flow through the uterine cavity.

While hysteroscopic resection can be effective in removing uterine fibroids, many commercially available instrument are too large in diameter and thus require anesthesia in an operating room environment. Conventional resectoscopes require cervical dilation to about 9 mm. What is needed is a system that can effectively cut and remove fibroid tissue through a small diameter hysteroscope.

SUMMARY OF THE INVENTION

The present invention provides improved systems and methods for managing fluid delivery to body spaces, such as a patient's uterus and other body cavities, during the performance of therapeutic or diagnostic medical procedures. The systems will include a fluid source, such as a saline intravenous (IV) fluid bag; fluid lines, such as tubes; conduits; medical flow connectors, such as luers and touhy borst valves; and a filter. Usually, at least one pump will be provided for delivering of a fluid from the fluid source to the body space, and recirculate back to the fluid source after passing through the filter.

Methods according to the present invention will comprise delivering the fluid to the body cavity and performing a therapeutic or a diagnostic procedure while the fluid distends the body cavity. Body materials, such as blood and tissue debris, are typically released into the fluid and the fluid is then recovered from the body cavity and passed through a filter to remove the body materials. The filtered fluid may then be returned to the fluid source where it is available for recirculation to the patient.

In a first specific aspect of the present invention, the filter comprises a hollow fiber filter assembly including a plurality of hollow fibers where the fluid passes through a lumen of each fiber and outwardly through the porous hollow fiber body to remove at least a portion of the contaminating body materials. Preferably, an additional filter element will be provided, usually upstream of the hollow fiber filter, where the contaminated body fluid will pass first through the additional filter element which is configured to capture tissue debris resulting from tissue resection and pass next through the hollow fiber filter which removes blood and remaining body materials from the recirculating distention fluid.

In specific examples, the hollow fibers will have a total lumen surface area of at least about 0.10 m2, usually at least 0.25 $m^2$, often at least 0.50 $m^2$, and frequently at least 1 $m^2$. The additional filter will typically have a pore size which is less than the diameter of the hollow fiber filters. For example, the pore size of the additional filter will typically be less than 150 microns while the hollow fiber filters will have a diameter of 200 microns or less. The hollow fibers will also have a nominal molecular weight limit (NMWL) of less than 40 kDa, usually less than 30 kDa, and often less than 20 kDa.

In a second aspect of the present invention, the fluid medical management system will comprise a filter including a plurality of hollow fibers having lumens and at least an additional filter element. A first fluid line is configured to carry a distention fluid from a fluid source to a body space, a second fluid line configured to carry the fluid from the body space to the filter, and a third fluid line configured to carry filtered fluid from the filter back to the fluid source. The filter element will have a pore size which is less than the diameter of the lumens of the hollow fibers, where the filter element has a pore size less than 150 microns and the hollow fibers have a diameter of less than 200 microns. In the specific embodiments, the system will further comprise a tissue-cutting tool, and the second fluid line will be configured to carry fluid and tissue debris such as cut tissue through the tissue cutting tool from the body space. The first filter will also typically be configured for decoupling from the system to allow the filter to be removed for transporting cut tissue for pathology or other purposes.

In a third aspect of the present invention, the fluid management system comprises a first fluid line, a second fluid line, and a third fluid line. A first pump is configured to carry distention fluid from a fluid source through the first line to a body space. A second pump is configured to deliver fluid from the body space through the second line and through the filter. The filtered fluid is then directed through the third fluid line from the filter back to the fluid source. The system further comprises a controller and a pressure sensor. The pressure sensor is located in a flow path communicating with the body cavity and provides intra-cavity pressure signals to the controller. The controller is configured to control the first and second pumps to maintain a selected pressure in the body cavity in response to the intra-cavity pressure signals. In preferred aspects, the controller operates the first pump at a variable rate and the second pump at a fixed rate, where control of the first pump rate provides the desired pressure control.

In a fourth aspect of the present invention, a medical fluid management system comprises a fluid source having an initial volume, where the initial volume represents the volume of saline or other distention fluid present in the fluid source prior to operation of the system. The system further comprises a filter having a fluid retention volume, where the retention volume is the amount of fluid which will be retained in the filter during operation of the system. The fluid will not be present in the filter prior to operation of the system. The system further comprises a first fluid line, a second fluid, and a third fluid line. The first fluid line is configured to carry distention fluid from the fluid source to a body space, and the second and third fluid lines are configured to recirculate fluid from the body space, through the filter and back to the fluid source. Each of the first fluid line, second fluid line and third fluid line will have retention volumes which represent the amount of recirculating fluid which will be retained in each of the fluid lines during operation of the system. A controller monitors the difference between (1) the initial volume of the fluid source which is present in the system prior to operation and (2) a sum of the volume of fluid in the fluid source present at any given time (which will be less than that initially present since some of the fluid will be in the fluid lines and filters and some will be resident in the patient) and the combined fluid retention volumes of the first line, second line, third line, and filter. By monitoring the difference, the amount of fluid which is resident in the patient at any given time can be followed. If the amount of fluid present in the patient exceeds an expected maximum amount, it can be determined that there is a substantial risk of intravasion. The system can then react by shutting down, providing an alarm, or both.

Typically, the preselected volume of fluid in the patient which is not to be exceeded will be 2.5 liters. The combined fluid retention volumes of first line, second line, third line, and filter will typically be about 0.5 liters. The material and structure of the hollow fibers may be any of the structures described above, typically including hollow fibers having a total lumen surface area of at least 0.10 m² and a NMWL of less than 40 kDa.

In a fifth aspect of the present invention, the medical fluid management system comprises a filter including both a first tissue-capture filter and a second hollow fiber filter. The first fluid line is configured to carry distention fluid from a fluid source to a body space. Second and third fluid lines are configured to recirculate fluid from the body space through the filter assembly and back to the fluid source. At least one check valve will be positioned intermediate the first and second filters to prevent backflow of fluid from the hollow fiber filter to the first filter. In specific embodiments, the system will comprise a fourth fluid line joining the first tissue-capture filter and the second hollow fiber filter, where the check valve is present in the fourth line. In further specific aspects, the first filter is configured for de-coupling from the system to allow removal of cut tissue. The first filter is also preferably configured to allow transport of the cut tissue after the filter has been decoupled from the system. In still further specific aspects, at least one additional check valve may be provided in the second fluid line to prevent backflow of fluid from the first filter to the body and a further additional check valve may be provided in the first fluid line for preventing backflow of fluid from the body to the fluid source.

DETAILED DESCRIPTION

Figure 1:
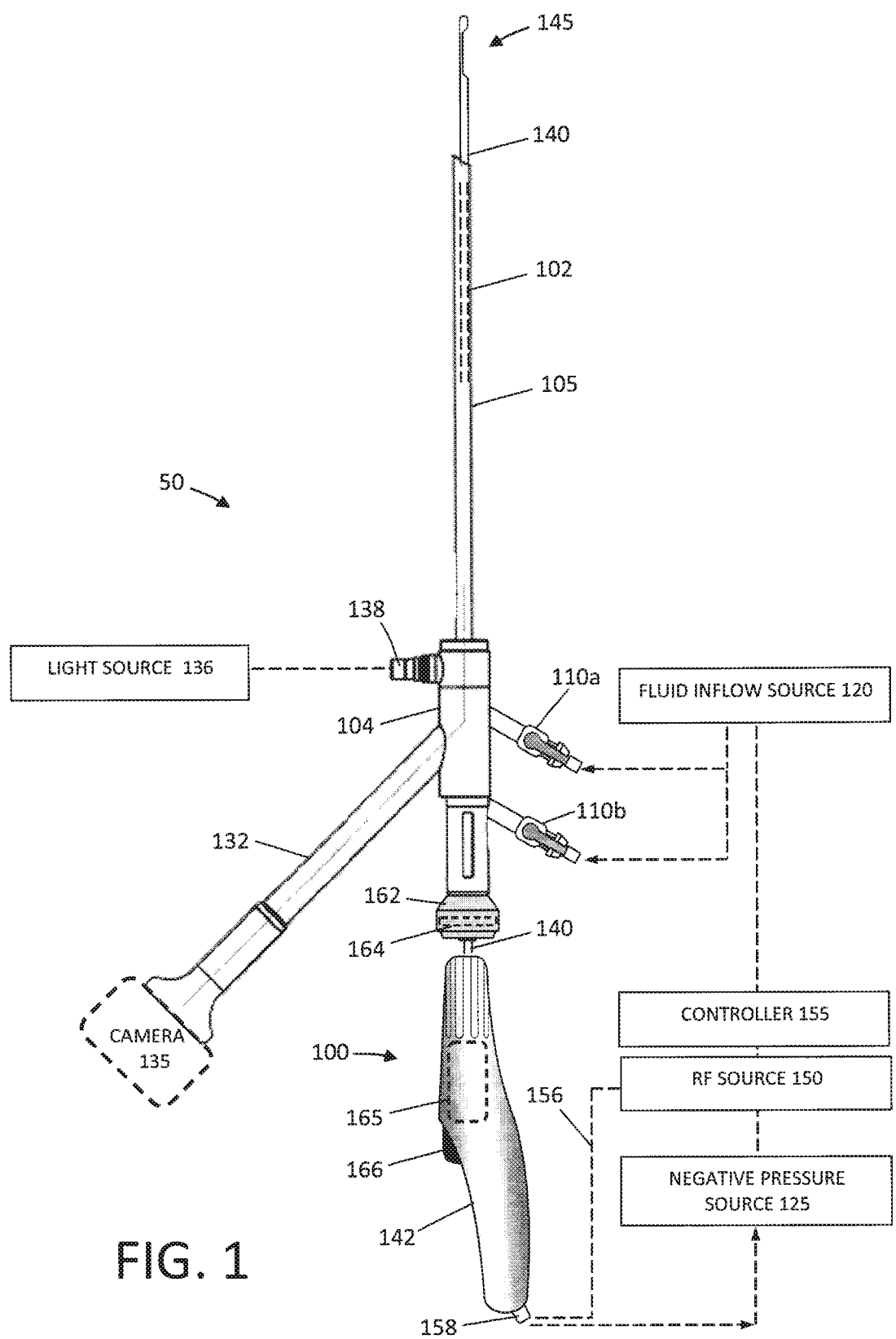
FIG. 1 is a plan view of an assembly including a hysteroscope and a tissue-cutting device corresponding to the invention that is inserted through the working channel of the hysteroscope.
Figure 2:
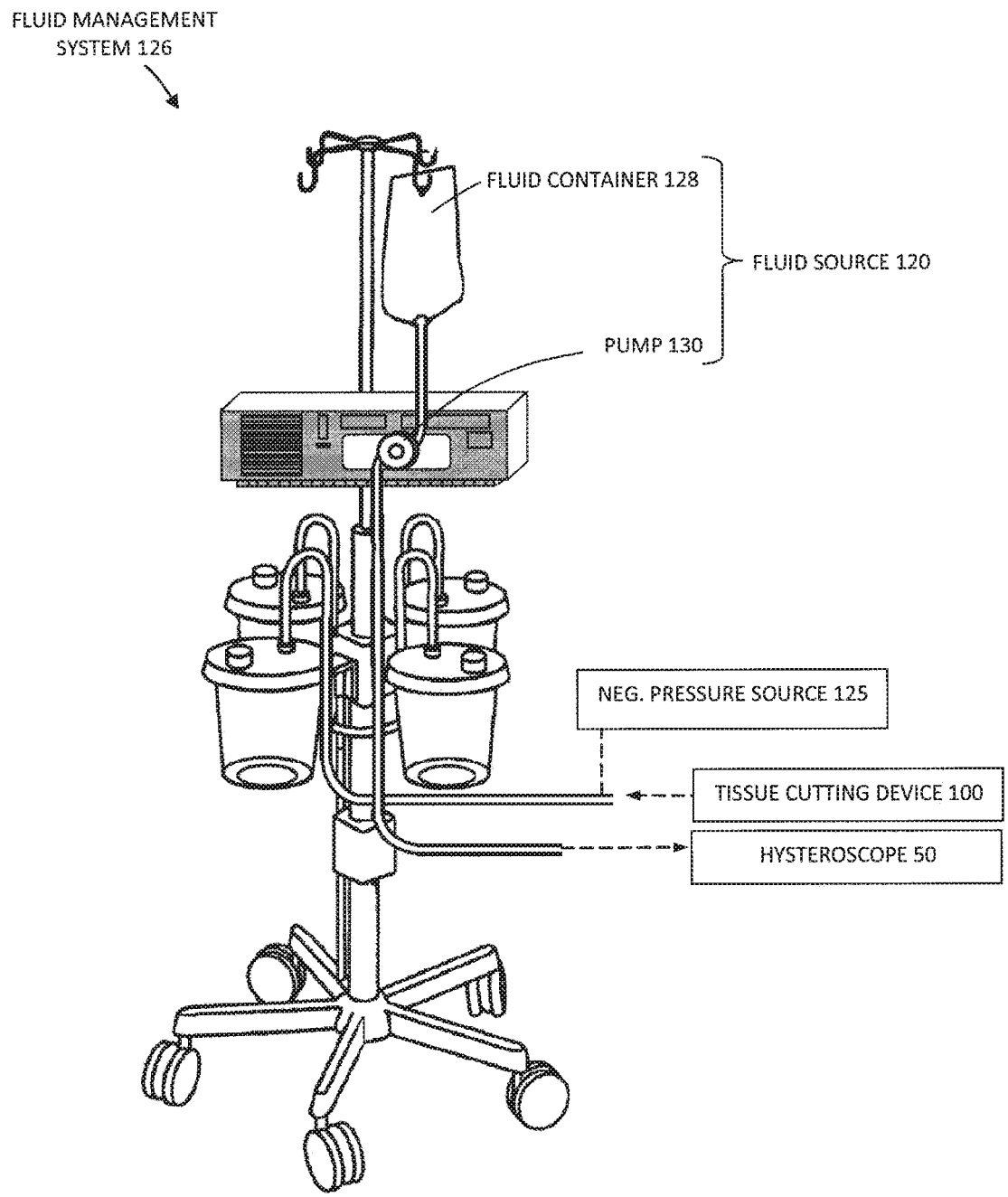
FIG. 2 is a schematic perspective view of a fluid management system used for distending the uterus and for assisting in electrosurgical tissue cutting and extraction

FIG. 1 illustrates an assembly that comprises an endoscope 50 used for hysteroscopy together with a tissue-extraction device 100 extending through a working channel 102 of the endoscope. The endoscope or hysteroscope 50 has a handle 104 coupled to an elongated shaft 105 having a diameter of 5 mm to 7 mm. The working channel 102 therein may be round, D-shaped or any other suitable shape. The endoscope shaft 105 is further configured with an optics channel 106 and one or more fluid inflow/outflow channels 108a, 108b (FIG. 3) that communicate with valve-connectors 110a, 110b configured for coupling to a fluid inflow source 120 thereto, or optionally a negative pressure source 125 (FIGS. 1-2). The fluid inflow source 120 is a component of a fluid management system 126 as is known in the art (FIG. 2) which comprises a fluid container 128 and pump mechanism 130 which pumps fluid through the hysteroscope 50 into the uterine cavity. As can be seen in FIG. 2, the fluid management system 126 further includes the negative pressure source 125 (which can comprise an operating room wall suction source) coupled to the tissue-cutting device 100. The handle 104 of the endoscope includes the angled extension portion 132 with optics to which a videoscopic camera 135 can be operatively coupled. A light source 136 also is coupled to light coupling 138 on the handle of the hysteroscope 50. The working channel 102 of the hysteroscope is configured for insertion and manipulation of the tissue-cutting and extracting device 100, for example to treat and remove fibroid tissue. In one embodiment, the hysteroscope shaft 105 has an axial length of 21 cm, and can comprise a 0° scope, or 15° to 30° scope.

Still referring to FIG. 1, the tissue-cutting device 100 has a highly elongated shaft assembly 140 configured to extend through the working channel 102 in the hysteroscope. A handle 142 of the tissue-cutting device 100 is adapted for manipulating the electrosurgical working end 145 of the device. In use, the handle 142 can be manipulated both rotationally and axially, for example, to orient the working end 145 to cut targeted fibroid tissue. The tissue-cutting device 100 has subsystems coupled to its handle 142 to enable electrosurgical cutting of targeted tissue. A radio frequency generator or RF source 150 and controller 155 are coupled to at least one RF electrode carried by the working end 145 as will be described in detail below. In one embodiment shown in FIG. 1, an electrical cable 156 and negative pressure source 125 are operatively coupled to a connector 158 in handle 142. The electrical cable couples the RF source 150 to the electrosurgical working end 145. The negative pressure source 125 communicates with a tissue-extraction channel 160 in the shaft assembly 140 of the tissue extraction device 100 (FIG. 4).

FIG. 1 further illustrates a seal housing 162 that carries a flexible seal 164 carried by the hysteroscope handle 104 for sealing the shaft 140 of the tissue-cutting device 100 in the working channel 102 to prevent distending fluid from escaping from a uterine cavity.

In one embodiment as shown in FIG. 1, the handle 142 of tissue-cutting device 100 includes a motor drive 165 for reciprocating or otherwise moving a cutting component of the electrosurgical working end 145 as will be described below. The handle 142 optionally includes one or more actuator buttons 166 for actuating the device. In another embodiment, a footswitch can be used to operate the device. In one embodiment, the system includes a switch or control mechanism to provide a plurality of reciprocation speeds, for example 1 Hz, 2 Hz, 3 Hz, 4 Hz and up to 8 Hz. Further, the system can include a mechanism for moving and locking the reciprocating cutting sleeve in a non-extended position and in an extended position. Further, the system can include a mechanism for actuating a single reciprocating stroke.

Figure 4:
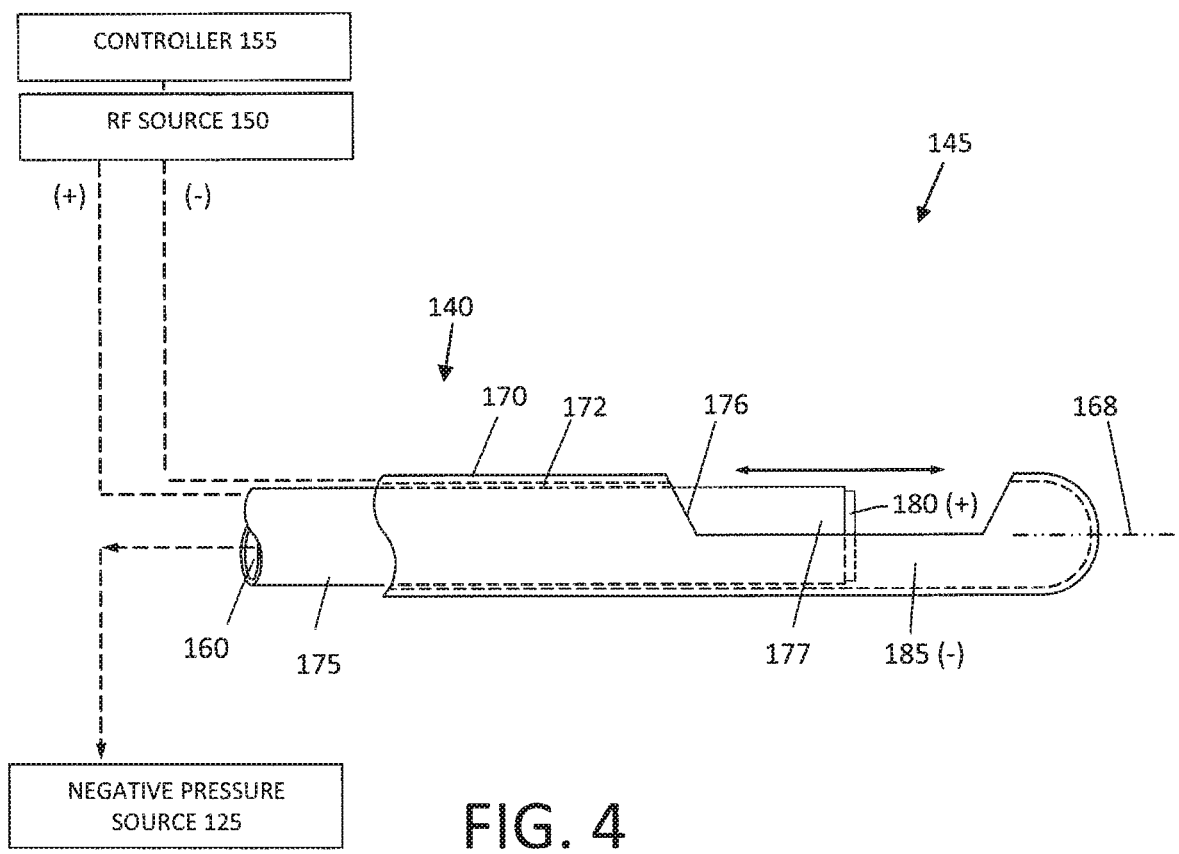
FIG. 4 is a schematic side view of the working end of the electrosurgical tissue-cutting device of FIG. 1 showing an outer sleeve and a reciprocating inner sleeve and an electrode arrangement.

Referring to FIGS. 1 and 4, an electrosurgical tissue-cutting device has an elongate shaft assembly 140 extending about longitudinal axis 168 comprising an exterior or first outer sleeve 170 with passageway or lumen 172 therein that accommodates a second or inner sleeve 175 that can reciprocate (and optionally rotate or oscillate) in lumen 172 to cut tissue as is known in that art of such tubular cutters. In one embodiment, the tissue-receiving window 176 in the outer sleeve 170 has an axial length ranging between 10 mm and 30 mm and extends in a radial angle about outer sleeve 170 from about 45° to 210° relative to axis 168 of the sleeve. The outer and inner sleeves 170 and 175 can comprise a thin-wall stainless steel material and function as opposing polarity electrodes as will be described in detail below. FIGS. 6A-8 illustrate insulative layers carried by the outer and inner sleeves 170 and 175 to limits, control and/or prevent unwanted electrical current flows between certain portions go the sleeve. In one embodiment, a stainless steel outer sleeve 170 has an O.D. of 0.143" with an I.D. of 0.133" and with an inner insulative layer (described below) the sleeve has a nominal I.D. of 0.125". In this embodiment, the stainless steel inner sleeve 175 has an O.D. of 0.120" with an I.D. of 0.112". The inner sleeve 175 with an outer insulative layer has a nominal O.D. of about 0.123" to 0.124" to reciprocate in lumen 172. In other embodiments, outer and or inner sleeves can be fabricated of metal, plastic, ceramic of a combination thereof. The cross-section of the sleeves can be round, oval or any other suitable shape.

As can be seen in FIG. 4, the distal end 177 of inner sleeve 175 comprises a first polarity electrode with distal cutting electrode edge 180 about which plasma can be generated. The electrode edge 180 also can be described as an active electrode during tissue cutting since the electrode edge 180 then has a substantially smaller surface area than the opposing polarity or return electrode. In one embodiment in FIG. 4, the exposed surfaces of outer sleeve 170 comprises the second polarity electrode 185, which thus can be described as the return electrode since during use such an electrode surface has a substantially larger surface area compared to the functionally exposed surface area of the active electrode edge 180.

Figure 5:
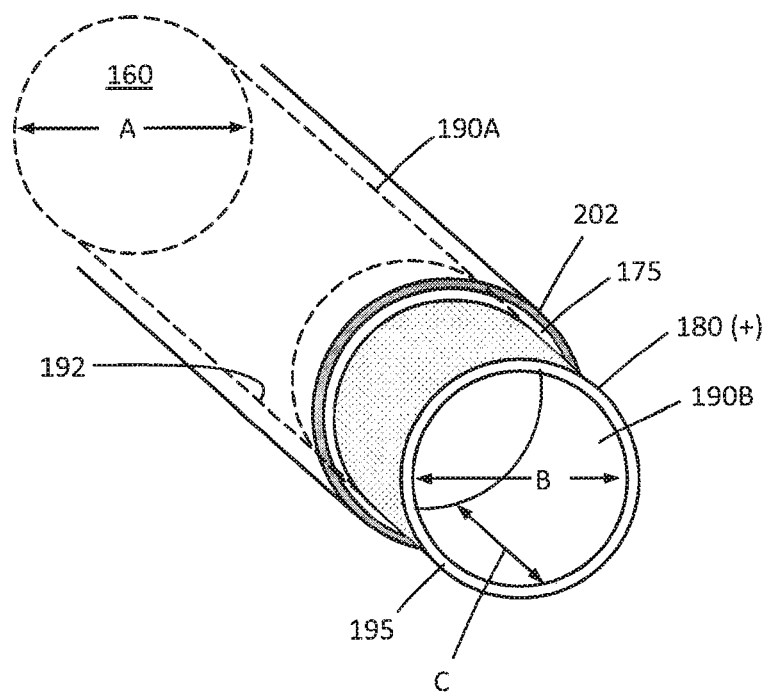
FIG. 5 is a schematic perspective view of the working end of the inner sleeve of FIG. 4 showing its electrode edge.
Figure 6A:
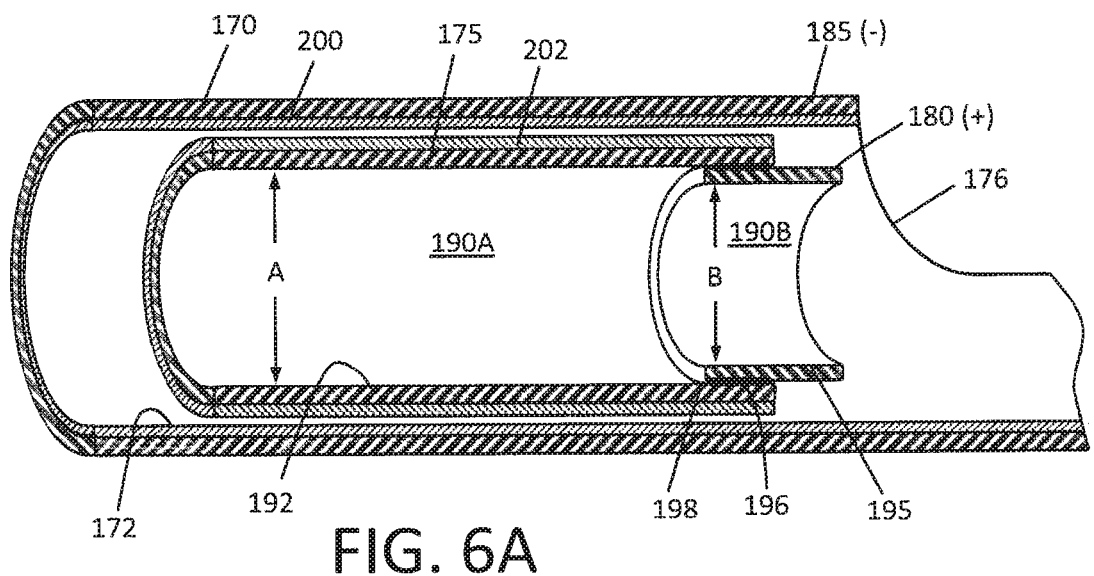
FIG. 6A is a schematic cut-away view of a portion of outer sleeve, inner RF cutting sleeve and a tissue-receiving window of the outer sleeve.

In one aspect of the invention, the inner sleeve or cutting sleeve 175 has an interior tissue extraction lumen 160 with first and second interior diameters that are adapted to electrosurgically cut tissue volumes rapidly—and thereafter consistently extract the cut tissue strips through the highly elongated lumen 160 without clogging. Now referring to FIGS. 5 and 6A, it can be seen that the inner sleeve 175 has a first diameter portion 190A that extends from the handle 142 (FIG. 1) to a distal region 192 of the sleeve 175 wherein the tissue extraction lumen transitions to a smaller second diameter lumen 190B with a reduced diameter indicated at B which is defined by the electrode sleeve element 195 that provides cutting electrode edge 180. The axial length C of the reduced cross-section lumen 190B can range from about 2 mm to 20 mm. In one embodiment, the first diameter A is 0.112" and the second reduced diameter B is 0.100". As shown in FIG. 5, the inner sleeve 175 can be an electrically conductive stainless steel and the reduced diameter electrode portion also can comprise a stainless steel electrode sleeve element 195 that is welded in place by weld 196 (FIG. 6A). In another alternative embodiment, the electrode and reduced diameter electrode sleeve element 195 comprises a tungsten tube that can be press fit into the distal end 198 of inner sleeve 175. FIGS. 5 and 6A further illustrates the interfacing insulation layers 202 and 204 carried by the first and second sleeves 170, 175, respectively. In FIG. 6A, the outer sleeve 170 is lined with a thin-wall insulative material 200, such as PFA, or another material described below. Similarly, the inner sleeve 175 has an exterior insulative layer 202. These coating materials can be lubricious as well as electrically insulative to reduce friction during reciprocation of the inner sleeve 175.

The insulative layers 200 and 202 described above can comprise a lubricious, hydrophobic or hydrophilic polymeric material. For example, the material can comprise a bio-compatible material such as PFA, TEFLON®, polytetrafluroethylene (PTFE), FEP (Fluorinated ethylenepropylene), polyethylene, polyamide, ECTFE (Ethylenechlorotrifluoroethylene), ETFE, PVDF, polyvinyl chloride or silicone.

Figure 6B:
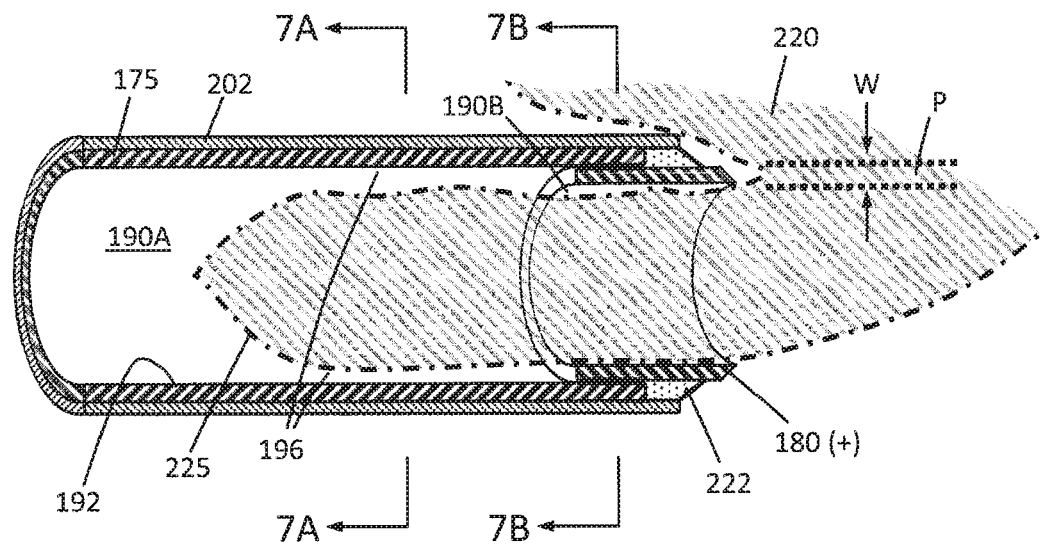
FIG. 6B is a schematic view of a distal end portion another embodiment of inner RF cutting sleeve.

Now turning to FIG. 6B, another variation of inner sleeve 175 is illustrated in a schematic view together with a tissue volume being resected with the plasma electrode edge 180. In this embodiment, as in other embodiments in this disclosure, the RF source operates at selected operational parameters to create a plasma around the electrode edge 180 of electrode sleeve 195 as is known in the art. Thus, the plasma generated at electrode edge 180 can cut and ablate a path P in the tissue 220, and is suited for cutting fibroid tissue and other abnormal uterine tissue. In FIG. 6B, the distal portion of the cutting sleeve 175 includes a ceramic collar 222 which is adjacent the distal edge 180 of the electrode sleeve 195. The ceramic 222 collar functions to confine plasma formation about the distal electrode edge 180 and functions further to prevent plasma from contacting and damaging the polymer insulative layer 202 on the cutting sleeve 175 during operation. In one aspect of the invention, the path P cut in the tissue 220 with the plasma at electrode edge 180 provides a path P having an ablated width indicated at W, wherein such path width W is substantially wide due to tissue vaporization. This removal and vaporization of tissue in path P is substantially different than the effect of cutting similar tissue with a sharp blade edge, as in various prior art devices. A sharp blade edge can divide tissue (without cauterization) but applies mechanical force to the tissue and may prevent a large cross section slug of tissue from being cut. In contrast, the plasma at the electrode edge 180 can vaporize a path P in tissue without applying any substantial force on the tissue to thus cut larger cross sections or slugs strips of tissue. Further, the plasma cutting effect reduces the cross section of tissue strip 225 received in the tissue-extraction lumen 190B. FIG. 6B depicts a tissue strip to 225 entering lumen 190B which has such a smaller cross-section than the lumen due to the vaporization of tissue. Further, the cross section of tissue 225 as it enters the larger cross-section lumen 190A results in even greater free space 196 around the tissue strip 225. Thus, the resection of tissue with the plasma electrode edge 180, together with the lumen transition from the smaller cross-section (190B) to the larger cross-section (190A) of the tissue-extraction lumen 160 can significantly reduce or eliminate the potential for successive resected tissue strips 225 to clog the lumen. Prior art resection devices with such small diameter tissue-extraction lumen typically have problems with tissue clogging.

Figure 7A:
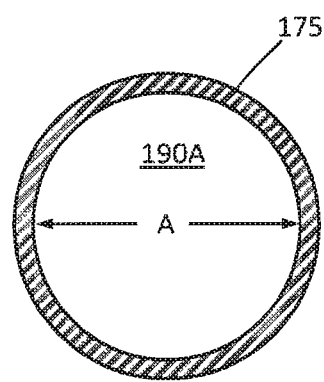
FIG. 7A is a cross sectional view of the inner RF cutting sleeve of FIG. 6B taken along line 7A-7A of FIG. 6B.
Figure 7B:
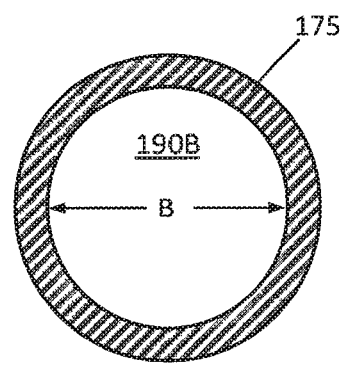
FIG. 7B is another cross sectional view of the inner RF cutting sleeve of FIG. 6B taken along line 7B-7B of FIG. 6B.
Figure 8:
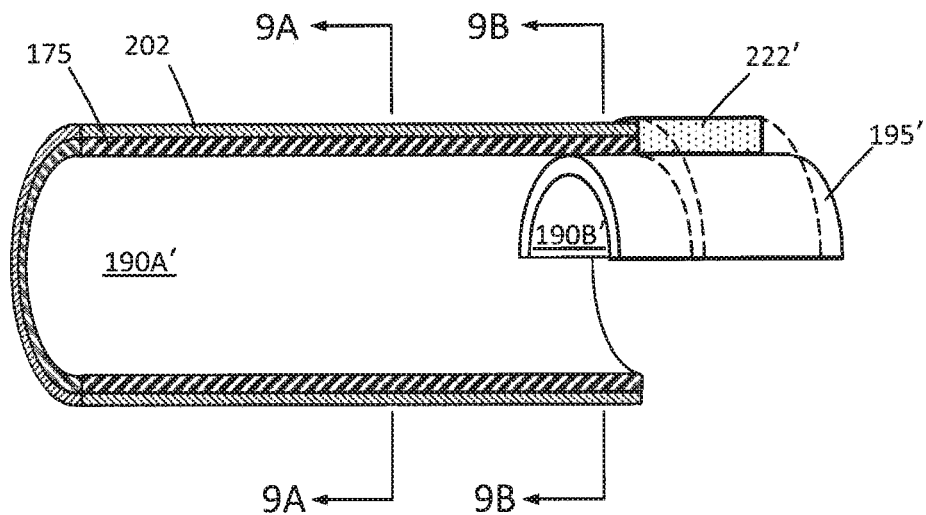
FIG. 8 is a schematic view of a distal end portion of another embodiment of inner RF cutting sleeve.
Figure 9A:
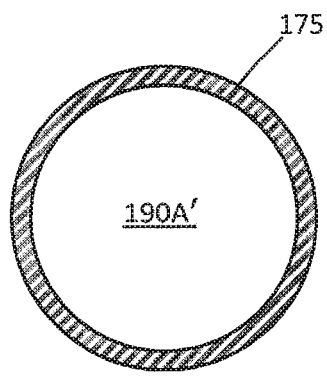
FIG. 9A is a cross sectional view of the RF cutting sleeve of FIG. 8 taken along line 9A-9A of FIG. 8.
Figure 9B:
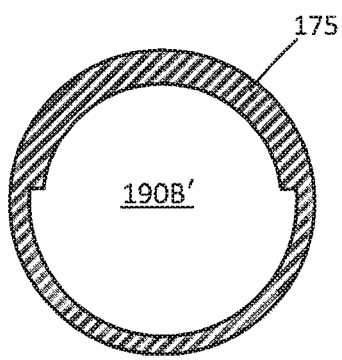
FIG. 9B is a cross sectional view of the RF cutting sleeve of FIG. 8 taken along line 9B-9B of FIG. 8.

In another aspect of the invention, the negative pressure source 225 coupled to the proximal end of tissue-extraction lumen 160 (see FIGS. 1 and 4) also assists in aspirating and moving tissue strips 225 in the proximal direction to a collection reservoir (not shown) outside the handle 142 of the device FIGS. 7A-7B illustrate the change in lumen diameter of cutting sleeve 175 of FIG. 6B. FIG. 8 illustrates the distal end of a variation of cutting sleeve 175' which is configured with an electrode cutting element 195' that is partially tubular in contrast to the previously described tubular electrode element 195 (FIGS. 5 and 6A). FIGS. 9A-9B again illustrate the change in cross-section of the tissue-extraction lumen between reduced cross-section region 190B' and the increased cross-section region 190A' of the cutting sleeve 175' of FIG. 8. Thus, the functionality remains the same whether the cutting electrode element 195' is tubular or partly tubular. In FIG. 8A, the ceramic collar 222' is shown, in one variation, as extending only partially around sleeve 175 to cooperate with the radial angle of cutting electrode element 195'. Further, the variation of FIG. 8 illustrates that the ceramic collar 222' has a larger outside diameter than insulative layer 202. Thus, friction may be reduced since the short axial length of the ceramic collar 222' interfaces and slides against the interfacing insulative layer 200 about the inner surface of lumen 172 of outer sleeve 170.

In general, one aspect of the invention comprises a tissue cutting and extracting device (FIGS. 10A-11C) that includes first and second concentric sleeves having an axis and wherein the second (inner) sleeve 175 has an axially-extending tissue-extraction lumen therein, and wherein the second sleeve 175 is movable between axially non-extended and extended positions relative to a tissue-receiving window 176 in first sleeve 170 to resect tissue, and wherein the tissue extraction lumen 160 has first and second cross-sections. The second sleeve 175 has a distal end configured as a plasma electrode edge 180 to resect tissue disposed in tissue-receiving window 176 of the first sleeve 170. Further, the distal end of the second sleeve, and more particularly, the electrode edge 180 is configured for plasma ablation of a substantially wide path in the tissue. In general, the tissue-extraction device is configured with a tissue extraction lumen 160 having a distal end portion with a reduced cross-section that is smaller than a cross-section of medial and proximal portions of the lumen 160.

In one aspect of the invention, referring to FIGS. 7A-7B and 9A-9B, the tissue-extraction lumen 160 has a reduced cross-sectional area in lumen region 190A proximate the plasma cutting tip or electrode edge 180 wherein said reduced cross section is less that 95%, 90%, 85% or 80% than the cross sectional area of medial and proximal portions 190B of the tissue-extraction lumen, and wherein the axial length of the tissue-extraction lumen is at least 10 cm, 20 cm, 30 cm or 40 cm. In one embodiment of tissue-cutting device 100 for hysteroscopic fibroid cutting and extraction (FIG. 1), the shaft assembly 140 of the tissue-cutting device is 35 cm in length.

Figure 10A:
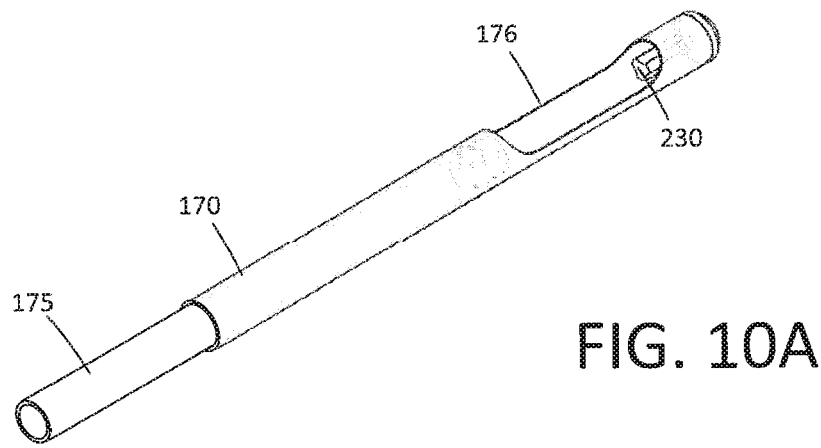
FIG. 10A is a perspective view of the working end of the tissue-cutting device of FIG. 1 with the reciprocating RF cutting sleeve in a non-extended position.
Figure 10B:
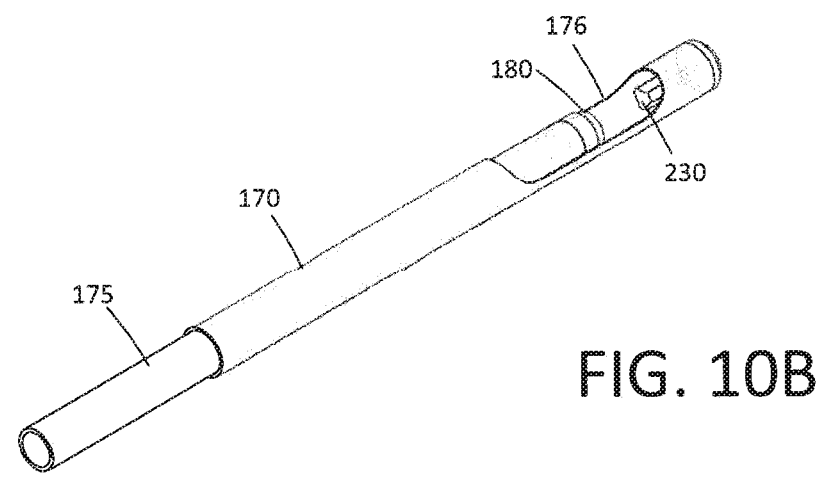
FIG. 10B is a perspective view of the tissue-cutting device of FIG. 1 with the reciprocating RF cutting sleeve in a partially extended position.
Figure 10C:
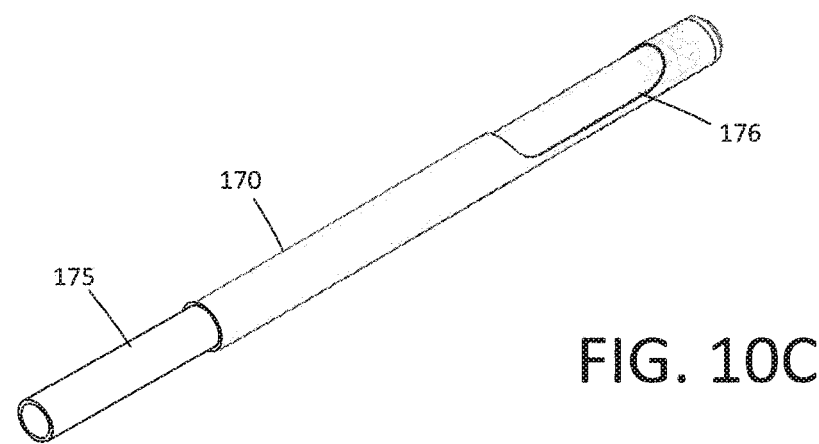
FIG. 10C is a perspective view of the tissue-cutting device of FIG. 1 with the reciprocating RF cutting sleeve in a fully extended position across the tissue-receiving window.
Figure 11A:
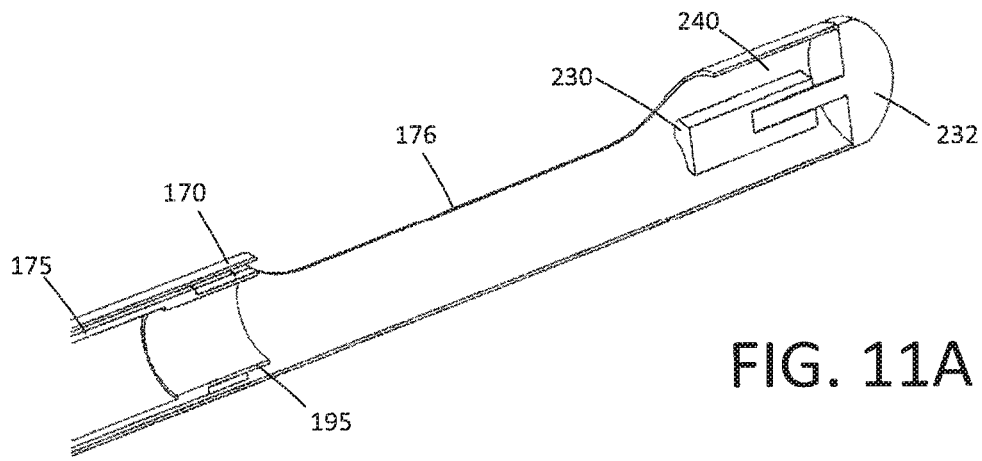
FIG. 11A is a sectional view of the working end of the tissue-cutting device of FIG. 10A with the reciprocating RF cutting sleeve in a non-extended position.
Figure 11B:
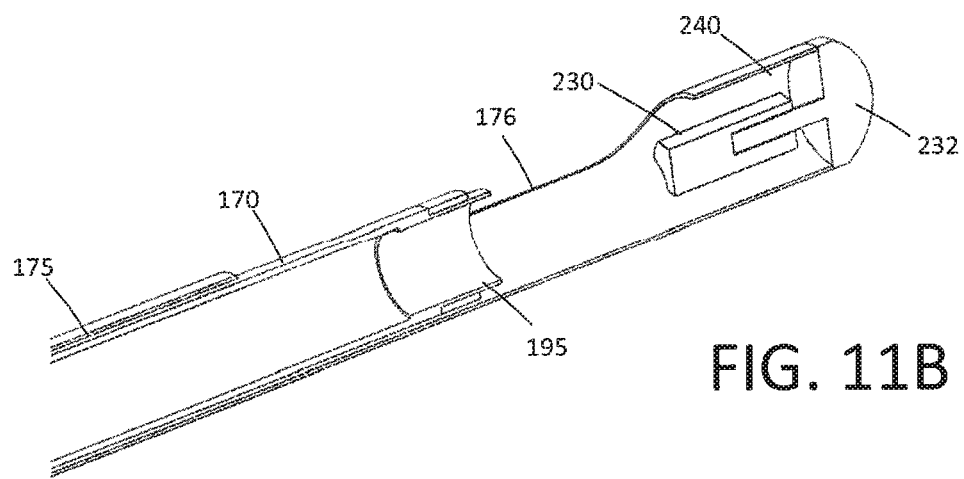
FIG. 11B is a sectional view of the working end of FIG. 10B with the reciprocating RF cutting sleeve in a partially extended position.
Figure 11C:
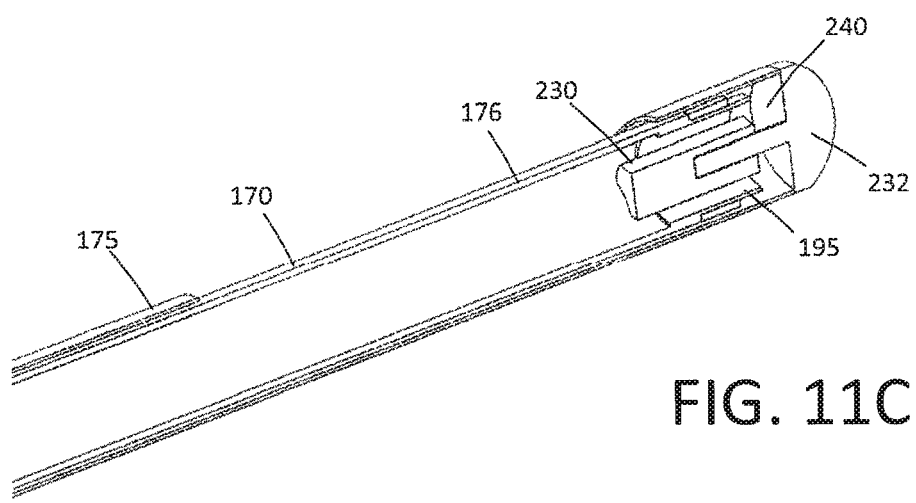
FIG. 11C is a sectional view of the working end of FIG. 10C with the reciprocating RF cutting sleeve in a fully extended position

FIGS. 10A-10C illustrate the working end 145 of the tissue-cutting device 100 with the reciprocating cutting sleeve or inner sleeve 175 in three different axial positions relative to the tissue receiving window 176 in outer sleeve 170. In FIG. 10A, the cutting sleeve 175 is shown in a retracted or non-extended position in which the sleeve 175 is at it proximal limit of motion and is prepared to advance distally to an extended position to thereby electrosurgically cut tissue positioned in and/or suctioned into in window 176. FIG. 10B shows the cutting sleeve 175 moved and advanced distally to a partially advanced or medial position relative to tissue cutting window 176. FIG. 10C illustrates the cutting sleeve 175 fully advanced and extended to the distal limit of its motion wherein the plasma cutting electrode 180 has extended past the distal end 226 of tissue-receiving window 176 at which moment the resected tissue strip 225 in excised from tissue volume 220 and captured in reduced cross-sectional lumen region 190A.

Now referring to FIGS. 10A-10C and FIGS. 11A-11C, another aspect of the invention comprises "tissue displacement" mechanisms provided by multiple elements and processes to "displace" and move tissue strips 225 in the proximal direction in lumen 160 of cutting sleeve 175 to thus ensure that tissue does not clog the lumen of the inner sleeve 175. As can be seen in FIG. 10A and the enlarged views of FIGS. 11A-11C, one tissue displacement mechanism comprises a projecting element 230 that extends proximally from distal tip 232 which is fixedly attached to outer sleeve 170. The projecting element 230 extends proximally along central axis 168 in a distal chamber 240 defined by outer sleeve 170 and distal tip 232. In one embodiment depicted in FIG. 11A, the shaft-like projecting element 230, in a first functional aspect, comprises a mechanical pusher that functions to push a captured tissue strip 225 proximally from the small cross-section lumen 190B of cutting sleeve 175 as the cutting sleeve 175 moves to its fully advanced or extended position. In a second functional aspect, the chamber 240 in the distal end of sleeve 170 is configured to capture a volume of saline distending fluid 244 from the working space, and wherein the existing RF electrodes of the working end 145 are further configured to explosively vaporize the captured fluid 244 to generate proximally-directed forces on tissue strips 225 resected and disposed in lumen 160 of the cutting sleeve 175. Both of these two functional elements and processes (tissue displacement mechanisms) can apply a substantial mechanical force on the captured tissue strips 225 by means of the explosive vaporization of liquid in chamber 240 and can function to move tissue strips 225 in the proximal direction in the tissue-extraction lumen 160. It has been found that using the combination of multiple functional elements and processes can virtually eliminate the potential for tissue clogging the tissue extraction lumen 160.

Figure 12A:
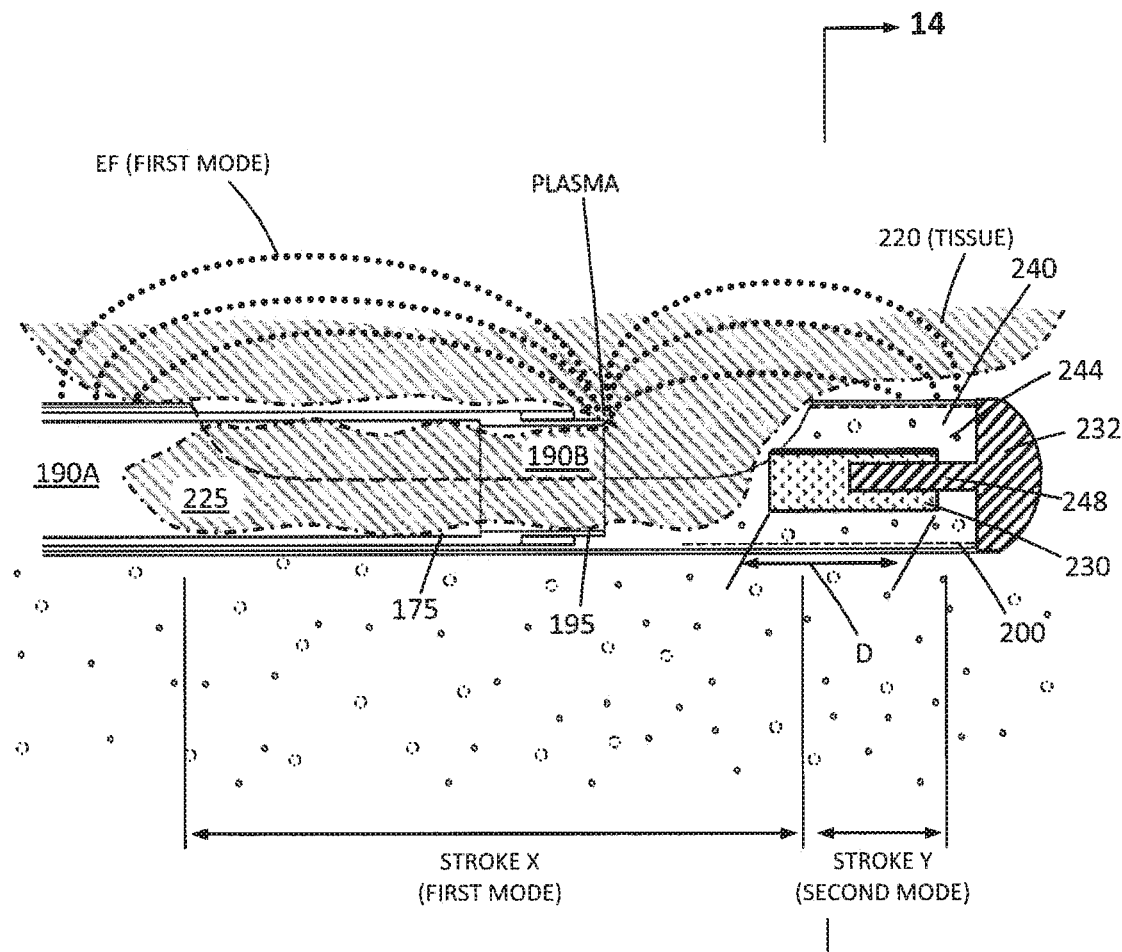
FIG. 12A is an enlarged sectional view of the working end of tissue-cutting device of FIG. 11B with the reciprocating RF cutting sleeve in a partially extended position showing the RF field in a first RF mode and plasma cutting of tissue.
Figure 12B:
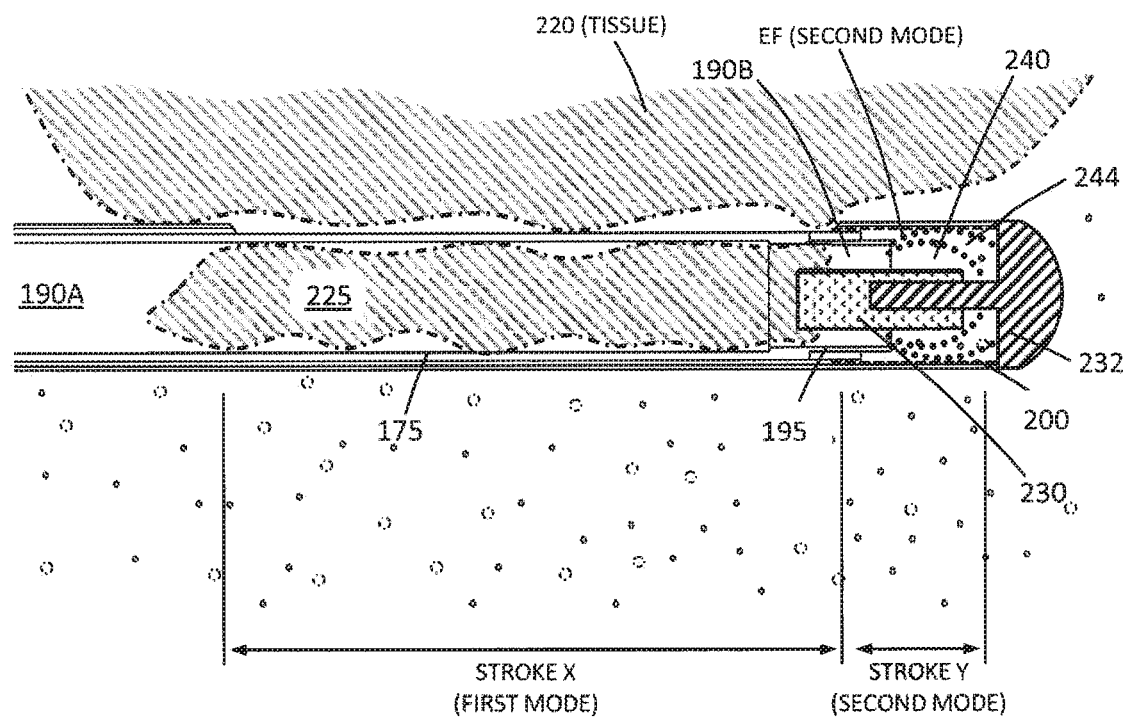
FIG. 12B is an enlarged sectional view of the working end of FIG. 11C with the reciprocating RF cutting sleeve almost fully extended and showing the RF fields switching to a second RF mode from a first RF mode shown in FIG. 12.
Figure 12C:
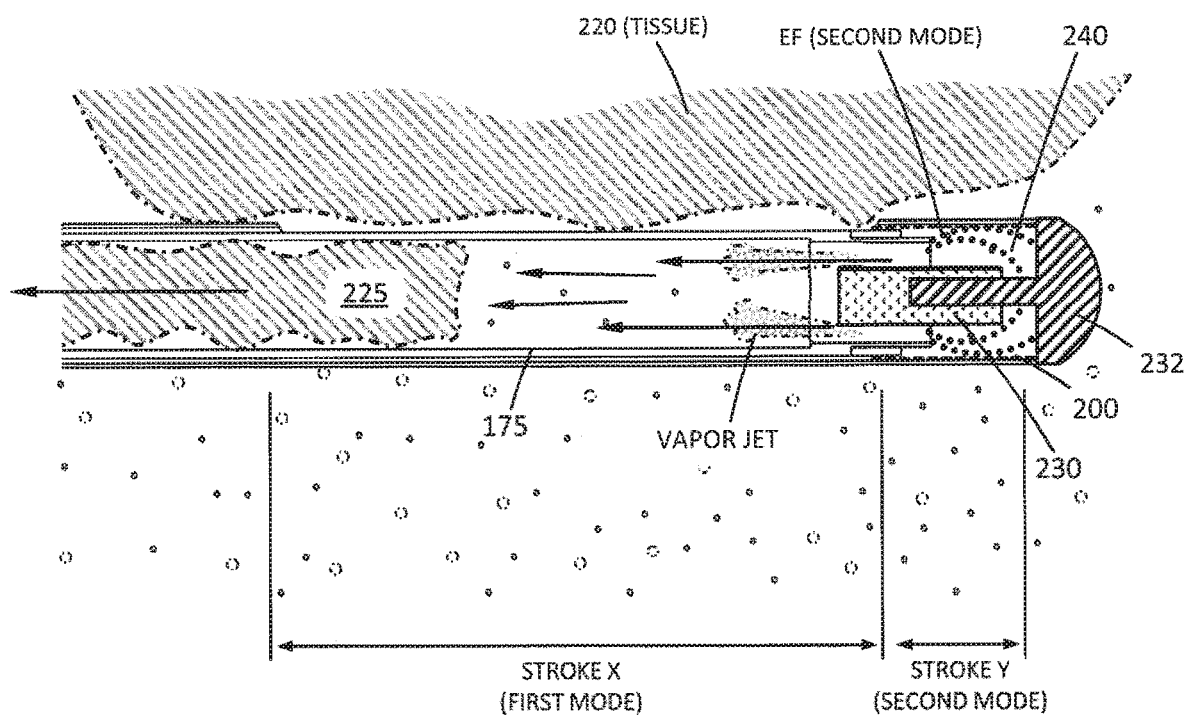
FIG. 12C is an enlarged sectional view of the working end of FIG. 11C with the reciprocating RF cutting sleeve again almost fully extended and showing the explosive vaporization of a captured liquid volume to expel cut tissue in the proximal direction.

More in particular, FIGS. 12A-12C illustrate sequentially the functional aspects of the tissue displacement mechanisms and the explosive vaporization of fluid captured in chamber 240. In FIG. 12A, the reciprocating cutting sleeve 175 is shown in a medial position advancing distally wherein plasma at the cutting electrode edge 180 is cutting a tissue strip 225 that is disposed within lumen 160 of the cutting sleeve 175. In FIG. 12A-12C, it can be seen that the system operates in first and second electrosurgical modes corresponding to the reciprocation and axial range of motion of cutting sleeve 175 relative to the tissue-receiving window 176. As used herein, the term "electrosurgical mode" refers to which electrode of the two opposing polarity electrodes functions as an "active electrode" and which electrode functions as a "return electrode". The terms "active electrode" and "return electrode" are used in accordance with convention in the art—wherein an active electrode has a smaller surface area than the return electrode which thus focuses RF energy density about such an active electrode. In the working end 145 of FIGS. 10A-11C, the cutting electrode element 195 and its cutting electrode edge 180 must comprise the active electrode to focus energy about the electrode to generate the plasma for tissue cutting. Such a high-intensity, energetic plasma at the electrode edge 180 is needed throughout stroke X indicated in FIG. 12A-12B to cut tissue. The first mode occurs over an axial length of travel of inner cutting sleeve 175 as it crosses the tissue-receiving window 176, at which time the entire exterior surface of outer sleeve 170 comprises the return electrode indicated at 185. The electrical fields EF of the first RF mode are indicated generally in FIG. 12A.

Figure 14:
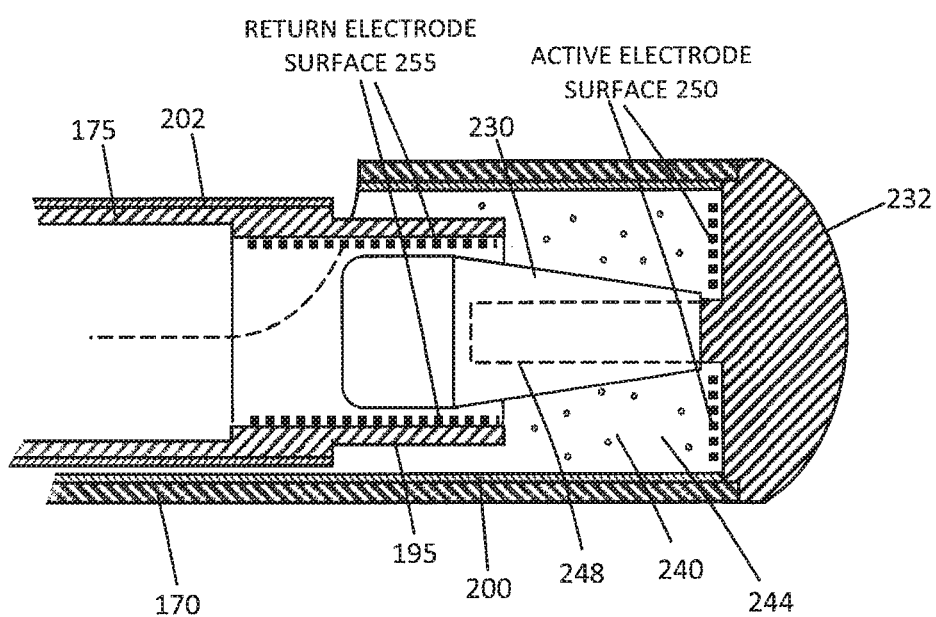
FIG. 14 is a sectional view of the working end of FIG. 12C showing an interior chamber and a variation of a projecting element.

FIG. 12B illustrates the moment in time at which the distal advancement or extension of inner cutting sleeve 175 entirely crossed the tissue-receiving window 176. At this time, the electrode sleeve 195 and its electrode edge 180 are confined within the mostly insulated-wall chamber 240 defined by the outer sleeve 170 and distal tip 232. At this moment, the system is configured to switch to the second RF mode in which the electric fields EF switch from those described previously in the first RF mode. As can be seen in FIG. 12B, in this second mode, the limited interior surface area 250 of distal tip 232 that interfaces chamber 240 functions as an active electrode and the distal end portion of cutting sleeve 175 exposed to chamber 240 acts as a return electrode. In this mode, very high energy densities occur about surface 250 and such a contained electric field EF can explosively and instantly vaporize the fluid 244 captured in chamber 240. The expansion of water vapor can be dramatic and can thus apply tremendous mechanical forces and fluid pressure on the tissue strip 225 to move the tissue strip in the proximal direction in the tissue extraction lumen 160. FIG. 12C illustrates such explosive or expansive vaporization of the distention fluid 244 captured in chamber 240 and further shows the tissue strip 225 being expelled in the proximal direction the lumen 160 of inner cutting sleeve 175. FIG. 14 further shows the relative surface areas of the active and return electrodes at the extended range of motion of the cutting sleeve 175, again illustrating that the surface area of the non-insulated distal end surface 250 is small compared to surface 255 of electrode sleeve which comprises the return electrode.

Still referring to FIGS. 12A-12C, it has been found that a single power setting on the RF source 150 and controller 155 can be configured both (i) to create plasma at the electrode cutting edge 180 of electrode sleeve 195 to cut tissue in the first mode, and (ii) to explosively vaporize the captured distention fluid 244 in the second mode. Further, it has been found that the system can function with RF mode-switching automatically at suitable reciprocation rates ranging from 0.5 cycles per second to 8 or 10 cycles per second. In bench testing, it has been found that the tissue-cutting device described above can cut and extract tissue at the rate of from 4 grams/min to 8 grams/min without any potential for tissue strips 225 clogging the tissue-extraction lumen 160. In one embodiment, a negative pressure source 125 can be coupled to the tissue-extraction lumen 160 to apply tissue-extracting forces to tissue strips in the lumen.

Of particular interest, the fluid-capture chamber 240 defined by sleeve 170 and distal tip 232 can be designed to have a selected volume, exposed electrode surface area, length and geometry to optimize the application of expelling forces to resected tissue strips 225. In one embodiment, the diameter of the chamber is 3.175 mm and the length is 5.0 mm which taking into account the projecting element 230, provided a captured fluid volume of approximately 0.040 mL. In other variations, the captured fluid volume can range from 0.004 to 0.080 mL.

In one example, a chamber 240 with a captured liquid volume of 0.040 mL together with 100% conversion efficiency in an instantaneous vaporization would require 103 Joules to heat the liquid from room temperature to water vapor. In operation, since a Joule is a W*s, and the system reciprocate at 3 Hz, the power required would be on the order of 311 W for full, instantaneous conversion to water vapor. A corresponding theoretical expansion of 1700× would occur in the phase transition, which would results in up to 25,000 psi instantaneously (14.7 psi×1700), although due to losses in efficiency and non-instantaneous expansion, the actual pressures would be less. In any event, the pressures are substantial and can apply expelling forces sufficient to the expel the captured tissue strips 225 the length of the extraction channel in the probe.

Figure 13:
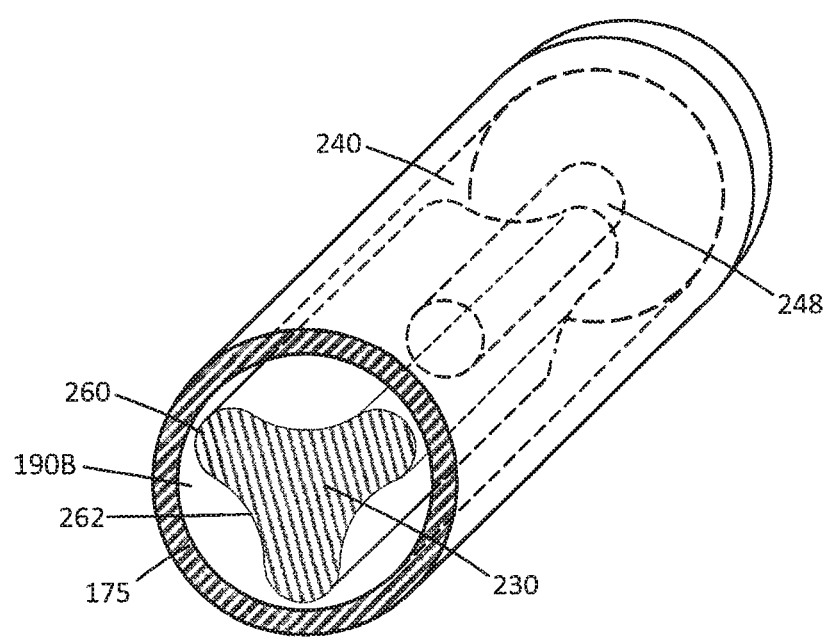
FIG. 13 is an enlarged perspective view of a portion of the working end of FIG. 12C showing an interior chamber and a fluted projecting element.

Referring to FIG. 12A, the interior chamber 240 can have an axial length from about 0.5 mm to 10 mm to capture a liquid volume ranging from about 0.004 mL 0.01 mL. It can be understood in FIG. 12A, that the interior wall of chamber 240 has an insulator layer 200 which thus limits the electrode surface area 250 exposed to chamber 240. In one embodiment, the distal tip 232 is stainless steel and is welded to outer sleeve 170. The post element 248 is welded to tip 232 or machined as a feature thereof. The projecting element 230 in this embodiment is a non-conductive ceramic. FIG. 13 shows the cross-section of the ceramic projecting element 230 which is fluted, which in one embodiment has three flute elements 260 in three corresponding axial grooves 262 in its surface. Any number of flutes, channels or the like is possible, for example from 2 to about 20. The purpose of this design is to provide a significant cross-sectional area at the proximal end of the projecting element 230 to push the tissue strip 225, while at the same time the three grooves 262 permit the proximally-directed jetting of water vapor to impact the tissue exposed to the grooves 262. In one embodiment, the axial length D of the projecting element 230 is configured to push tissue entirely out of the reduced cross-sectional region 190B of the electrode sleeve element 195. In another embodiment, the volume of the chamber 240 is configured to capture liquid that when explosively vaporized provided a gas (water vapor) volume sufficient to expand into and occupy at least the volume defined by a 10% of the total length of extraction channel 160 in the device, at least 20% of the extraction channel 160, at least 40% of the extraction channel 160, at least 60% of the extraction channel 160, at least 80% of the extraction channel 160 or at least 100% of the extraction channel 160.

As can be understood from FIGS. 12A to 12C, the distending fluid 244 in the working space replenishes the captured fluid in chamber 240 as the cutting sleeve 175 moves in the proximal direction or towards its non-extended position. Thus, when the cutting sleeve 175 again moves in the distal direction to cut tissue, the interior chamber 240 is filled with fluid 244 which is then again contained and is then available for explosive vaporization as described above when the cutting sleeve 175 closes the tissue-receiving window 176. In another embodiment, a one-way valve can be provided in the distal tip 232 to draw fluid directly into interior chamber 240 without the need for fluid to migrate through window 176.

Figure 15:
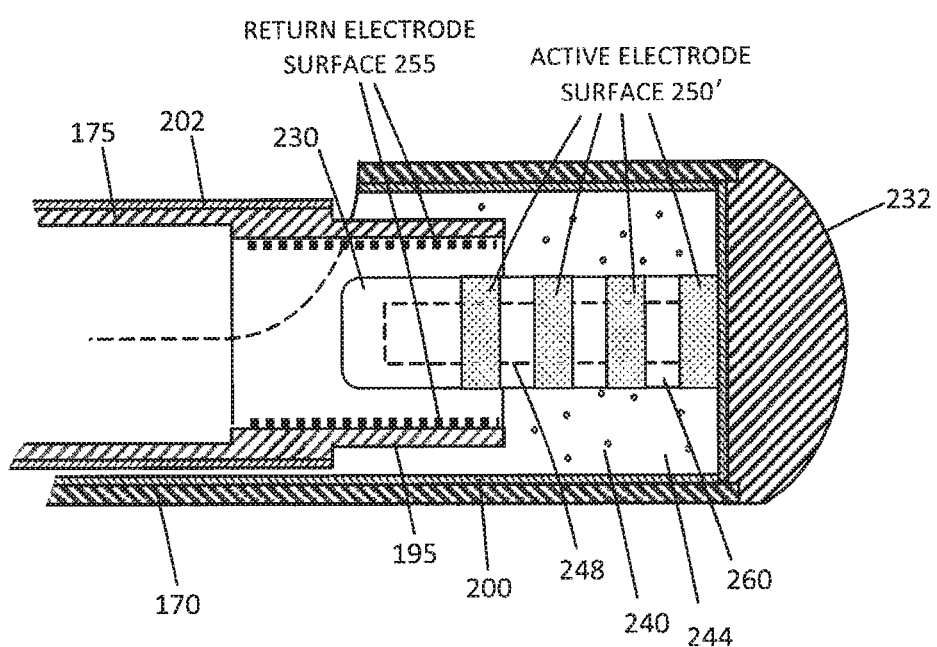
FIG. 15 is a sectional view of the working end of FIG. 12C showing an interior chamber and a variation of a projecting element configured to explosively vaporize the captured liquid volume.

FIG. 15 illustrates another variation in which the active electrode surface area 250' in the second mode comprises a projecting element 230 with conductive regions and non-conductive regions 260 which can have the effect of distributing the focused RF energy delivery over a plurality of discrete regions each in contact with the captured fluid 244. This configuration can more efficiently vaporize the captured fluid volume in chamber 240. In one embodiment, the conductive regions 250' can comprise metal discs or washers on post 248. In other variation (not shown) the conductive regions 250' can comprise holes, ports or pores in a ceramic material 260 fixed over an electrically conductive post 248.

In another embodiment, the RF source 150 and controller 155 can be programmed to modulate energy delivery parameters during stroke X and stroke Y in FIGS. 12A-12C to provide the optimal energy (i) for plasma cutting with electrode edge 180, and (ii) for explosively vaporizing the captured fluid in chamber 240.

Figure 16:
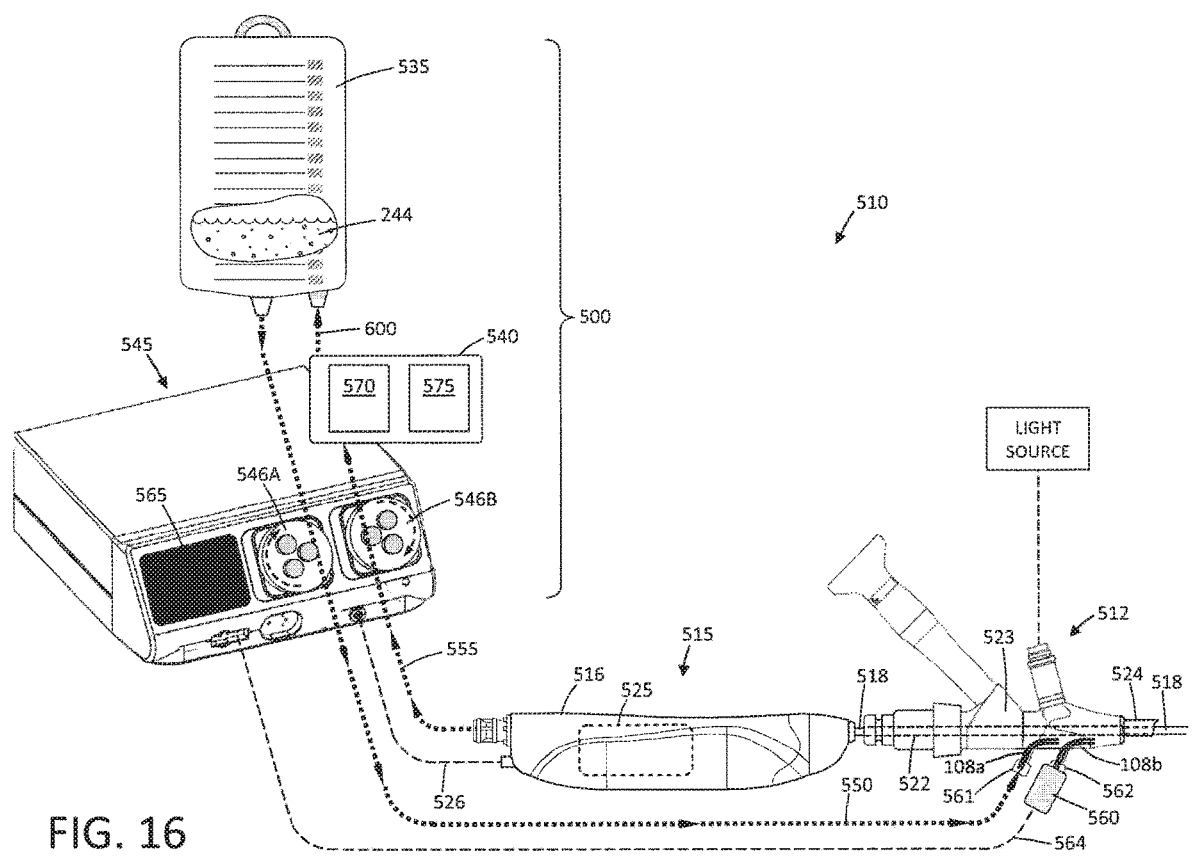
FIG. 16 is a schematic view of a system for fibroid removal including a fluid management system.
Figure 17:
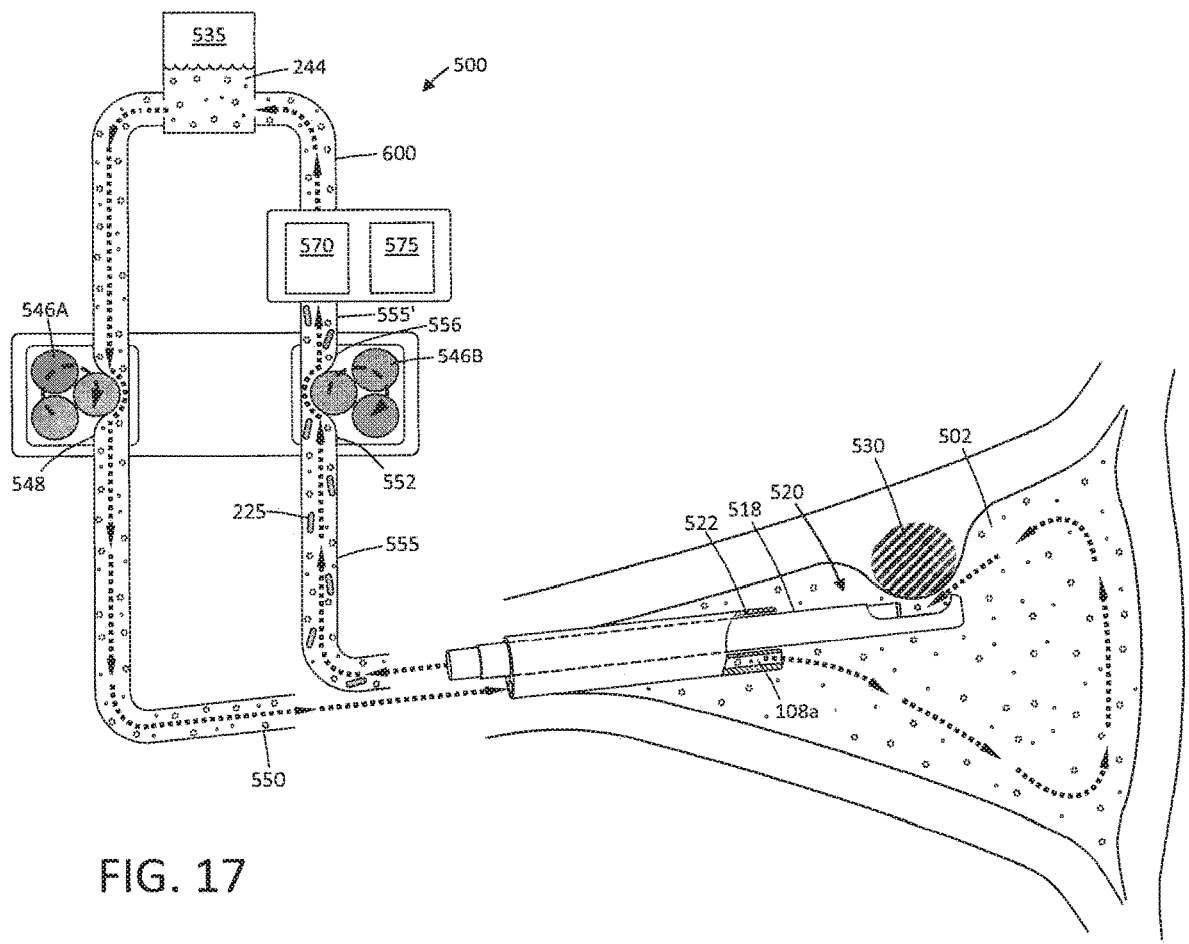
FIG. 17 is a schematic view of the fluid management system of FIG. 16 with an enlarged view of the working end of a tissue-cutting probe as generally described in FIGS. 1-12C in a position to cut and remove a fibroid.
Figure 18:
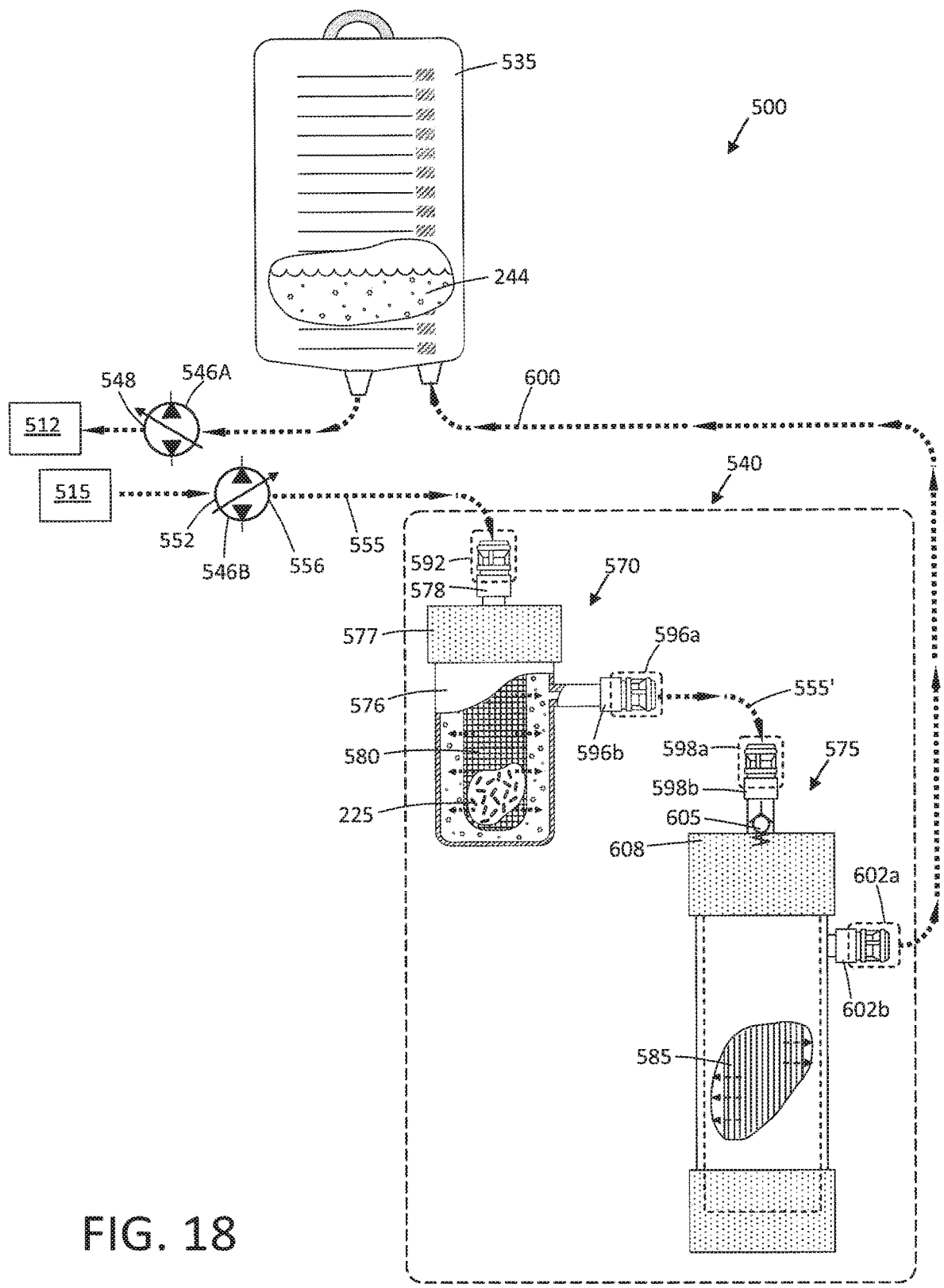
FIG. 18 is a cut-away schematic view of a filter module of the fluid management system of FIGS. 16-17.

FIGS. 16-18 illustrate a fluid management system 500 that can be used when treating tissue in a body cavity, space or potential space 502 (FIG. 17). The fluid management system 500 is depicted schematically in a hysteroscopic fibroid treatment system 510 that is adapted for cutting and extraction of fibroids or other abnormal intra-uterine tissue using a hysteroscope 512 and tissue-cutting probe 515 that can be similar to those described above. FIG. 16 depicts the tissue-cutting probe 515 with handle 516 and extension member 518 with working end 520 (FIG. 17) that can be introduced through working channel 522 extending through the body 523 and shaft 524 of the hysteroscope 512. FIG. 16 further shows a motor 525 in handle 516 of the tissue-cutting probe that is coupled to a controller and power supply by power cable 526. FIG. 17 illustrates the working end 520 of the cutting probe 515 in a uterine cavity proximate a targeted fibroid 530.

Referring to FIGS. 16-17, in general, the fluid management system 500 comprises a fluid source or reservoir 535 of a distention fluid 244, a controller and pump system to provide fluid inflows and outflows adapted to maintain distension of a body space and a filter system 540 for filtering distention fluid 244 that is removed from the body cavity and thereafter returned to the fluid source 535. The use of a recovered and filtered fluid 244 and the replenishment of the fluid source 535 is advantageous because (i) the closed-loop fluid management system can effectively measure fluid deficit to thereby monitor intravasation and insure patient safety, (ii) the system can be set up and operated in a very time-efficient manner, and (ii) the system can be compact and less expensive to thereby assist in enabling office-based procedures.

Figure 3:
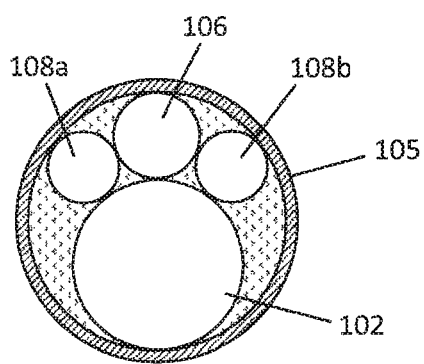
FIG. 3 is a cross-sectional view of the shaft of the hysteroscope of FIG. 1 showing various channels therein.

The fluid management system 500 (FIG. 16) includes a computer control system that is integrated with the RF control system in an integrated controller 545. The controller 545 is adapted to control first and second peristaltic pumps 546A and 546B for providing inflows and outflows of a distention fluid 244, such as saline solution, from source 535 for the purpose of distending the body cavity and controlling the intra-cavity pressure during a tissue cutting-extracting procedure as depicted in FIG. 17. In one embodiment shown in FIGS. 16-18, the controller 545 controls peristaltic pump 546A to provide positive pressure at the outflow side 548 of the pump (FIG. 17) to provide inflows of distention fluid 244 through first flow line 550 which is in communication with fitting 561 and fluid flow channel 108a in hysteroscope 515. The flow channel 108a is described above in a previous embodiment and is illustrated in FIG. 3 above. The controller 545 further controls the second peristaltic pump 546B to provide negative pressure at the inflow side 552 of the pump (FIG. 17) to the second line 555 to assist in providing outflows of distention fluid 244 from the body cavity 502. As described above, the explosive vaporization of fluid in the working end 525 of cutting probe 515 functions to expel tissue strips 225 proximally in the extraction channel 160 of cutting sleeve 175, which can operate in conjunction with negative pressures in line 555 provided by pump 546B. In operation, the second peristaltic pump 546B also operates to provide positive pressure on the outflow side 556 of pump 546B in the second flow line portion 555' to pump outflows of distention fluid 244 through the filter system 540 and back to the fluid source 535.

In one system embodiment, the controller 545 operates to control pressure in cavity 502 by pressure signals from a pressure sensor 560 that is coupled to a fitting 562 in hysterocope 512 which communicates with a flow channel 108b (see FIG. 16) that extends through the hysteroscope. In one embodiment, the flow channel 108b has a diameter of at least 1.0 mm to allow highly accurate sensing of actual intra-cavity pressure. In prior art commercially-available fluid management systems, the intra-cavity pressure is typically estimated by various calculations using known flow rates through a pump or remote pressure sensors in the fluid inflow line that can measure back pressures. Such prior art fluid management systems are stand-alone systems and are adapted for use with a wide variety of hysteroscopes and endoscopes, most of which do not have a dedicated flow channel for communicating with a pressure sensor. For this reason, prior art fluid management systems rely on algorithms and calculations to only estimate intra-cavity pressure.

In one embodiment, as depicted in FIG. 16, the pressure sensor 560 is disposable and is operatively coupled to controller 545 by cable 564. In one embodiment, the sensor can be a piezoresistive silicon pressure sensor, Model No. 1620, available from Measurement Specialties. Ltd., 45738 Northport Loop West, Fremont, Calif. 94538.

FIG. 17 schematically illustrates the fluid management system 500 in operation. The uterine cavity 502 is a potential space and needs to be distended to allow for hysteroscopic viewing. A selected pressure can be set in the controller 545, for example via a touch screen 565, which the physician knows from experience is suited for distending the cavity 502 and/or for performing a procedure. In one embodiment, the selected pressure can be any pressure between 0 and 150 mm Hg. In one system embodiment, the first pump 546A can operate as a variable speed pump that is actuated to provide a flow rate of up to 850 ml/min through first line 550. In this embodiment, the second pump 546B can operate at a fixed speed to move fluid in the second line 555. In use, the controller 545 can operate the pumps 546A and 546B at selected matching or non-matching speeds to increase, decrease or maintain the volume of distention fluid 244 in the uterine cavity 502. Thus, by independent control of the pumping rates of the first and second peristaltic pumps 546A and 546B, a selected set pressure in the body cavity can be achieved and maintained in response to signals of actual intra-cavity pressure provided by sensor 560.

In one system embodiment, as shown in FIGS. 17-18, the fluid management system 500 includes a filter module or system 540 that can include a first filter or tissue-capturing filter 570 that is adapted to catch tissue strips 225 that have been cut and extracted from the body cavity 502. A second filter or molecular filter 575, typically a hollow fiber filter, is provided beyond the first filter 570, wherein the molecular filter 575 is adapted to remove blood and other body materials from the distention fluid 244. In particular, the molecular filter 575 is capable of removing red blood cells, hemoglobin, particulate matter, proteins, bacteria, viruses and the like from the distention fluid 244 so that endoscopic viewing of the body cavity is not obscured or clouded by any such blood components or other contaminants. As can be understood from FIGS. 16-18, the second peristaltic pump 546B at its outflow side 556 provides a positive pressure relative to fluid flows into the filter module 540 to move the distention fluid 244 and body media through the first and second filters, 570 and 575, and in a circulatory flow back to the fluid source 535.

Referring to FIG. 18, in an embodiment, the first filter 570 comprises a container portion or vial 576 with a removable cap 577. The inflow of distention fluid 244 and body media flows through line portion 555 and through fitting 578 into a mesh sac or perforate structure 580 disposed in the interior chamber 582 of the vial 576. The pore size of the perforate structure 580 can range from about 200 microns to 10 microns. The lumen diameter of hollow fibers 585 in the second filter 575 can be from about 400 microns to 20 microns. In general, the pore size of perforate structure 580 in the first filter 570 is less than the diameter of the lumens of hollow fibers 585 in the second filter 575. In one embodiment, the pore size of the perforate structure 580 is 100 microns, and the lumen size of the hollow fibers 585 in the molecular filter 575 is 200 microns. In one embodiment, the molecular filter 575 is a Nephros DSU filter available from Nephros, Inc., 41 Grand Ave., River Edge, N.J. 07661. In one variation, the filter 575 is configured with hollow fibers having a nominal molecular weight limit (NMWL) of less than 50 kDa, 30 kDa or 20 kDa.

In another aspect of the invention, the molecular filter 575 is configured to filter large volumes of distention fluid, since the fluid flows are circulating. Additionally, the molecular filter 575 is configured to filter significant potential volumes of distention fluid that may contaminated with blood, blood products and the like that will be mixed with the fluid. In one embodiment, the molecular filter 575 has a membrane surface area of at least 0.6 m$^2$, 0.8 m$^2$, 1.0 m$^2$, 1.2 m$^2$ and 1.4 m$^2$, wherein the membrane surface area is defined as the total surface area of the lumens of the hollow fibers 585 in the molecular filter 575. In another aspect of the invention, a method of fluid management can include distending a body space and maintaining a flow rate of up to 850 ml/min of a distension fluid flow into and out of a body space and thereafter through a filter system 540 capable of removing at least 20 ml, 40 ml or 60 ml of blood from the distension fluid 244.

Referring to FIG. 18, it can be seen that the filter module 540 includes detachable connections between the various fluid flow lines to allow for rapid coupling and de-coupling of the filters and flow lines. More in particular, flow line 555 extending from the tissue-cutting probe 515 has a connector portion 592 that connects to inlet fitting 578 in the first filter 546A. Flow line portion 555' that is intermediate the filters 546A and 546B has connector portion 596a that connects to outlet fitting 596b in first filter 542A. The outflow end of flow line 555' has connector 598a that connects to inlet fitting 598b of the second filter 546B. The return flow line 600 that is intermediate the second 546B and fluid source 535 has connector portion 602a that connects to outlet fitting 602b in second first filter 546B. In one embodiment, at least one check valve 605 is provided in the flow path intermediate the filters 546A, 546B which for example can be in line 555', connectors 596a, 598a or fittings 596b, 598b. In FIG. 18, a check valve 605 is integrated with the inlet end 608 of the second filter 546B. In use, the operation of the system will result in substantial fluid pressures in the interior of the second filter, and the check valve 605 allows for de-coupling the first filter without escape of pressure and release of fluid media into the environment, for example, when the tissue cutting procedure is completed and the physician or nurse wishes to transport the vial 576 and tissue strips 225 therein to a different site for biopsy purposes.

In one aspect, a fluid management system comprising a first fluid line 550 configured to carry distention fluid 224 or influent from a fluid source 535 to a body space, a second fluid line 555, 555' and 560 configured to carry fluid from the body space to a first filter 570 and then to a second filter 575 and then back to the fluid source 535, a pump operatively coupled to the second fluid line to move the fluid and at least one check valve 605 in the second fluid line intermediate the first and second filters 570 and 575.

In one embodiment, the controller 545 of the fluid management system 500 is configured for calculation of a fluid deficit that is measured as a difference between a fluid volume delivered to the body space 502 and a fluid volume recovered from the body space during a medical procedure such as fibroid removal (see FIGS. 16-17). A method of fluid management in a hysteroscopic procedure comprises providing a distention fluid source 535 (FIG. 17) having a predetermined volume, introducing fluid (e.g., saline) from the source 535 through a first flow path or line 550 into the uterine cavity and through a second flow line 555 out of the cavity into a filter module 540 and through a further portion 600 of the second flow line back to the fluid source 535 wherein the interior volume of the first and second flow lines and the filter module when subtracted from the predetermined volume of the source 535 equals 2.5 liters or less to thereby insure that saline intravasion is less than 2.5 liters. In this variation, the predetermined volume of the source 535 can be 3.0 liters, as in a standard 3 liter saline bag, and the interior system volume can be at least 0.5 liters.

While certain embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A medical fluid management system, comprising:
a fluid source having an initial volume;
a filter system having a fluid retention volume;
a first fluid line configured to carry distention fluid from the fluid source to a body space, said first fluid line having a fluid retention volume;
second and third fluid lines configured to re-circulate fluid from the body space through the filter system and back to the fluid source, said second and third fluid lines having a fluid retention volume;
an inflow pump configured to deliver distention fluid from the fluid source through the first fluid line to the body space;
an outflow pump configured to deliver distention fluid from the body space through the filter system and second and third fluid lines back to the fluid source;
a controller configured to control the inflow and outflow pumps;
wherein the controller is configured to monitor a difference between (1) the initial volume of the fluid source and (2) a sum of a volume of fluid in the fluid source present at a given time and the combined fluid retention volumes of the filter system and first, second and third fluid lines;
wherein the controller is configured to sound an alarm and shut down the inflow and outflow pumps when the difference exceeds a preselected volume.

2. The system of claim 1, wherein the preselected volume is 2.5 liters.

3. The system of claim 2, wherein the combined fluid retention volumes of the filter system and first, second and third fluid lines is at least 0.5 liters.

4. The system of claim 2, wherein the initial volume of the fluid source is 3 liters.

5. The system of claim 1, wherein the combined fluid retention volumes of the filter system and first, second and third fluid lines is at least 0.5 liters.

6. The system of claim 1, wherein the filter system includes a tissue capturing filter and a molecular filter.

7. The system of claim 6, further comprising a check valve fluidly coupled between the tissue capturing filter and the molecular filter.

8. The system of claim 6, wherein the check valve is located at an inlet of the molecular filter.

9. A medical fluid management system, comprising:
a fluid source having an initial volume;
a filter system having a fluid retention volume;
a first fluid line configured to carry distention fluid from the fluid source to a body space, said first fluid line having a fluid retention volume;
second and third fluid lines configured to re-circulate fluid from the body space through the filter system and back to the fluid source, said second and third fluid lines having a fluid retention volume;

an inflow pump configured to deliver distention fluid from the fluid source through the first fluid line to the body space;

an outflow pump configured to deliver distention fluid from the body space through the filter system and second and third fluid lines back to the fluid source;

a controller configured to control the inflow and outflow pumps;

wherein the controller is configured to monitor a difference between: (1) the initial volume of the fluid source; and (2) a sum of a volume of fluid in the fluid source present at a given time and the combined fluid retention volumes of the filter system and first, second and third fluid lines;

wherein the controller is configured to sound an alarm when the difference exceeds a preselected volume.

10. The system of claim 9, wherein the preselected volume is 2.5 liters.

11. The system of claim 10, wherein the combined fluid retention volumes of the filter system and first, second and third fluid lines is at least 0.5 liters.

12. The system of claim 10, wherein the initial volume of the fluid source is 3 liters.

13. The system of claim 9, wherein the combined fluid retention volumes of the filter system and first, second and third fluid lines is at least 0.5 liters.

14. The system of claim 9, wherein the filter system includes a tissue capturing filter and a molecular filter.

15. The system of claim 14, further comprising a check valve fluidly coupled between the tissue capturing filter and the molecular filter.

16. The system of claim 14, wherein the check valve is located at an inlet of the molecular filter.

17. A medical fluid management system, comprising:

a fluid source having an initial volume;

a filter system having a fluid retention volume;

a first fluid line configured to carry distention fluid from the fluid source to a body space, said first fluid line having a fluid retention volume;

second and third fluid lines configured to re-circulate fluid from the body space through the filter and back to the fluid source, said second and third fluid lines having a fluid retention volume; and a controller which monitors a difference between (1) the initial volume of the fluid source and (2) a sum of a volume of fluid in the fluid source present at a given time and the combined fluid retention volumes of the filter system and first, second and third fluid lines;

wherein the controller is configured to sound an alarm when the difference exceeds a preselected volume that indicates a risk of intravasion.

18. The system of claim 17, wherein the preselected volume is 2.5 liters.

19. The system of claim 18, wherein the combined fluid retention volumes of the filter system and first, second and third fluid lines is at least 0.5 liters.

20. The system of claim 18, wherein the initial volume of the fluid source is 3.0 liters.

* * * * *